(12) United States Patent
Mancini et al.

(10) Patent No.: US 11,117,918 B2
(45) Date of Patent: Sep. 14, 2021

(54) ENZYME-DIRECTED IMMUNOSTIMULANT AND USES THEREOF

(71) Applicant: Washington State University, Pullman, WA (US)

(72) Inventors: Rock Joseph Mancini, Pullman, WA (US); Amy Esther Nielsen, Pullman, WA (US); Joseph Daniel Hantho, Pullman, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 16/720,899

(22) Filed: Dec. 19, 2019

(65) Prior Publication Data

US 2020/0199166 A1 Jun. 25, 2020

Related U.S. Application Data

(62) Division of application No. 15/722,018, filed on Oct. 2, 2017, now abandoned.

(60) Provisional application No. 62/402,062, filed on Sep. 30, 2016.

(51) Int. Cl.
*C07H 15/26* (2006.01)
*A61K 31/706* (2006.01)
*A61K 47/54* (2017.01)
*A61P 35/00* (2006.01)

(52) U.S. Cl.
CPC ........... *C07H 15/26* (2013.01); *A61K 31/706* (2013.01); *A61K 47/549* (2017.08); *A61P 35/00* (2018.01)

(58) Field of Classification Search
CPC ..... C07H 15/26; A61K 31/706; A61K 47/549
See application file for complete search history.

(56) References Cited

PUBLICATIONS

Harris et al., Women's Health, 2007, 3(1), p. 15-27. (Year: 2007).*
Definition of phosphor, OED, https://www.oed.com, accessed online on Jan. 12, 2021. (Year: 2021).*
Shukla et al., Bioorg. Med. Chem. Lett., 2010, 20, p. 6384-6386. (Year: 2010).*

* cited by examiner

*Primary Examiner* — Jonathan S Lau
(74) *Attorney, Agent, or Firm* — W & C IP

(57) ABSTRACT

The disclosed invention relates to the novel composition of matter that allows for the controlled release of highly active compounds to be delivered to a desired site. This novel composition utilizes the immune system to allow for the controlled release of desired compounds. The present invention can utilize a plurality of highly active compounds, with one embodiment being the use of chemotherapeutics for the treatment of cancer.

6 Claims, 7 Drawing Sheets

ENZYME-DIRECTED IMMUNOSTIMULANT AND USES THEREOF

CROSS-REFERENCE TO RELATED APPLICATION(S)

The present application is a divisional application of U.S. Ser. No. 15/722,018 filed Oct. 2, 2017, which itself claims under 35 U.S.C. § 119, the priority benefit of U.S. Provisional Application No. 62/402,062 filed Sep. 30, 2016. The disclosure of the foregoing provisional application is incorporated herein by reference in its entirety.

BACKGROUND OF THE INVENTION

Field of the Invention

This invention generally relates to a novel composition of matter that allows for the controlled release of highly active compounds to a desired site. This novel composition utilizes the immune system to control the release of the desired compound to effectively deliver the active agent to a desired site. While there are a plurality of applications for this technology, one embodiment examined herein is the compounds application as a chemotherapeutic in the treatment of cancer and multi-drug resistant cancer.

Discussion of the Related Art

Immunomodulators have been an area of study since the 13th century when it was observed that spontaneous regression of tumors occurred after the tumor became infected. As such, the deliberate infection of tumors followed by the subsequent immune response became common practice in the 18th and 19th centuries as a treatment option for cancer (Coley's Toxins). Since then there has been a good deal of research and effort dedicated to harnessing the immune response as a viable treatment for cancer.

While immunomodulators have been shown to have promise as a treatment option for cancer, one of the major obstacles to wide-spread adoption of the process is the manner in which the immune response is activated. It is known to those skilled in the art that drug delivery is a critical factor in both maintaining an effective dose of a compound and reducing off-target effects. Unfortunately, the pharmacokinetic properties of most drugs are such that they need to be administered multiple times a day or in large doses. This kind of dosing regimen is inconvenient and leads to reductions in patient compliance, especially for immunomodulators.

Drugs that are administered in traditional tablet or capsule form generally have a high infusion of the drug administered to the body followed by a rapid decline. For many drugs, this delivery pattern results in a transient overdose, followed by a long period of under dosing. These patterns of drug administration, while useful to specific drugs and formulations, have limited universal clinical usefulness when considering immunomodulators.

SUMMARY OF THE INVENTION

The present embodiments herein relate to a novel composition of matter that may be utilized, for example, as an Immunotherapeutic. This novel innovation allows for the delivery of immunomodulator to a desired site for the purposes of treating or preventing a disease state. The applications for such a technology allow for a plurality of treatment and prevention options but will notably allow for the treatment of disease states via the activation of the immune system.

In one aspect of the invention, a new family of compounds are described which have the structure of Formula I:

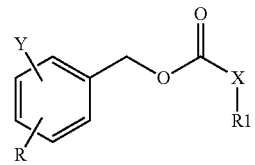

or a pharmaceutically acceptable salt thereof, wherein, X is O, S, CH2, or N and Y can be at one or more locations on the benzene ring, and may be the same or different at different locations, and is a substituent that modifies the electron density within the appended benzene ring consisting of groups optionally containing: hydrogen, nitro, alcohol, alkyl ether wherein with ether chain can be a repeating chain where n equals 5, alkyl ester wherein with ether chain can be a repeating chain where n equals 5, or a carboxylate.

R is an enzyme substrate such as a pyranose-like structure or alternatively it can be a furanose-like structure wherein the chiral centers can be independently racemic or in the S or R stereo configuration. Thus, compounds according to this aspect include combinations of stereo configuration, or mixtures thereof. Additional examples can also include glutamic acid or serine, examples of which can be selected from the compounds of the chemical formula:

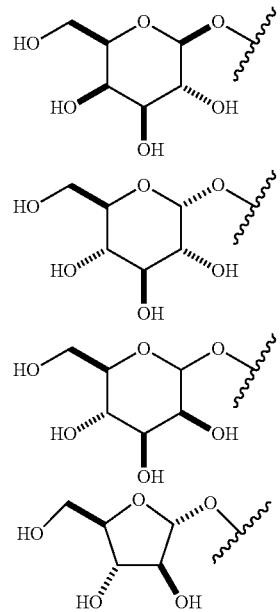

R1 is an immunomodulator that can function by enhancing the immune response at the site that it is released. This group of compounds can include, but are not limited to, known therapeutics such as interferons, or Imiquimod, but can also include cellular membrane fractions from bacteria or even chemotherapeutic agents. Some select examples of immunomodulators are selected from the compounds of the chemical formula:

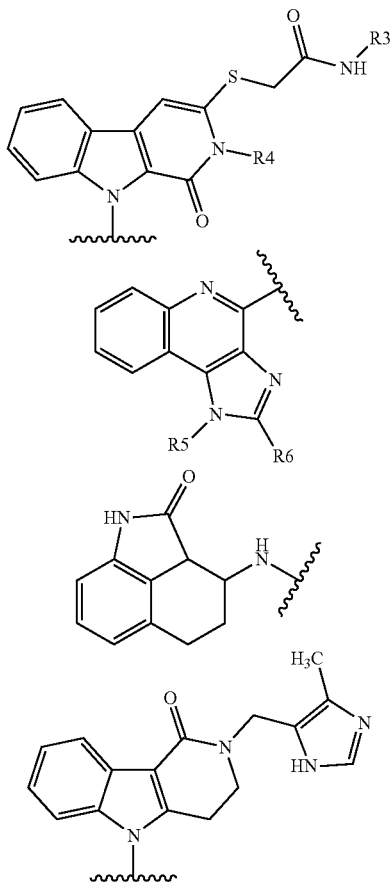

where R3 is aryl, substituted aryl, heteroaryl, substituted alkyl, akynyl, substituted and substituted alkynyl; R4 is aryl, substituted aryl, and heteroaryl; R5 is aryl, substituted aryl, alkyl, and substituted alkyl; and R6 is alkyl, substituted alkyl, alkynyl, and substituted alkynyl.

In another aspect of the invention, the compounds of Formula I, can be used in a method for treating a patient that would benefit from the controlled release of an immunomodulator for the treatment of a disease state or disorder. Disease states or disorders include, but are not limited to: cancer, multidrug-resistant cancer, multidrug-resistant pathogen infection, or comparable disease states resulting from under-activation of the immune system; or asthma, Crohn's disease, or a comparable disease state resulting from over-activation of the immune system.

The foregoing and other objects, features, and advantages of the present disclosure will become more apparent from the following detailed description, which proceeds with reference to the accompanying figures.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1A:
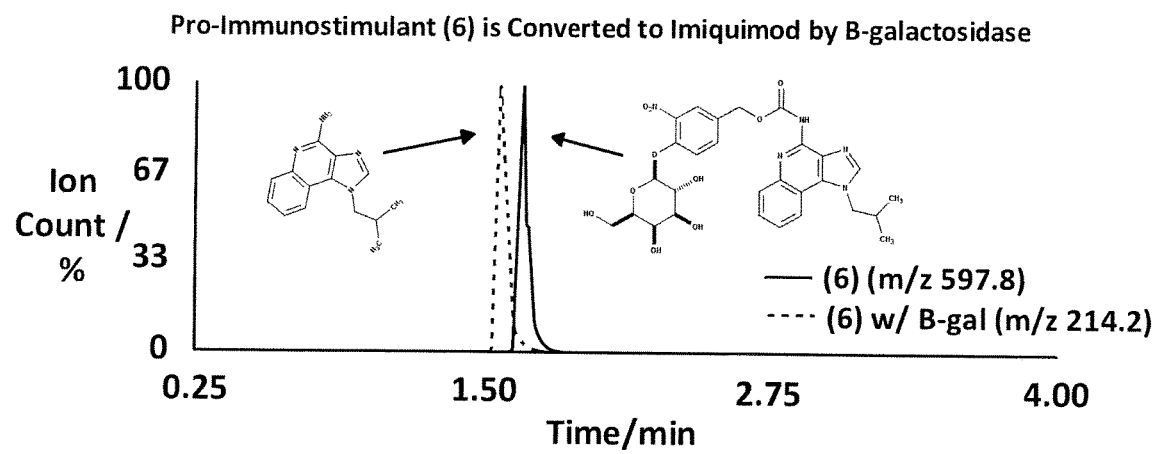
FIG. 1a shows the conversion of 2 nmol of immunomodulator measured by LC-MS/MS before and after addition of β-galactosidase resulting in quantitative conversion into Imiquimod.

The following are definitions of terms that may be used in the present specification. The initial definition provided for a group or term herein applies to that group or term throughout the present specification individually or as part of another group, unless otherwise indicated.

The term "immune-modulator" or "immunomodulator", by itself means a chemical species that induces the activation or increasing activity of any of the components in the immune system and/or inhibits the aforementioned activity. Examples of immunomodulators in the practice of invention can include immunostimulants such as imidazoquinolines.

The term "linker', by itself means a substructure that can contain an ester, carbonate, carbamate, xanthate, phosphate, nitroxide, serine, or alkyl, or aryl groups with functionality thereof, or alkyl or aryl groups with appended heteroatoms. In the practice of this invention, the substructure that is the linker will attach, for example, an immunostimulant group to an enzyme substrate group. The linker can be removed from the immunostimulant (or other immunomodulator) following conversion or removal of the enzyme substrate group.

The term "enzyme substrate", by itself or as part of another substituent means a chemical structure with at least one covalent bond that that has the capability of being broken by an enzyme.

The term "controlled release" (and variations of that phrase (e.g., in the context of "controlled-release system")) refers to release of a therapeutic agent (e.g., a drug such as a chemotherapeutic agent or immunotherapeutic agent) at a selected site at a controllable rate, within a controllable interval, and/or in a specified amount. "Controlled-release" encompasses, but is not necessarily limited to, substantially continuous delivery, metronomic delivery (e.g., intermittent delivery over a period of time that is interrupted by regular or irregular time intervals) or delivery of a bolus of a selected therapeutic agent (or various combinations thereof) as a predetermined, discrete amount over a relatively short period of time (e.g., a few seconds or minutes).

The term "therapeutic agent" refers to a controlled release immunomodulator that interactions locally at the site of release with the particular targeted site (e.g., a tumor).

The term "aryl" refers to monocyclic, bicyclic, or polycyclic aromatic hydrocarbon groups having 4 to 7 carbon atoms in the ring portion, such as phenyl, each of which may be substituted.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, aralkyl, halo, trifluoromethoxy, trifluoromethyl, alkanoyl, alkanoyloxy, aryloxy, aralkyloxy, amino, alkylamino, arylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like.

The term "heteroaryl" refers to an optionally substituted aromatic group, for example, which is a 4 to 7 membered monocyclic, 7 to 11 membered bicyclic, or 10 to 15 membered tricyclic ring system, which can contain a heteroatom and can contain a carbon atom-containing ring.

The term "saturated" refers to a chemical structure that does not contain any double or triple carbon-carbon bonds.

For example, a saturated cycloalkyl group as defined herein includes cyclohexyl, cyclopropyl and the like.

The term "unsaturated" refers to a chemical structure that contains at least one carbon-carbon multiple bond. For example, an unsaturated cycloalkyl group as defined herein includes cyclohexenyl, cyclopentenyl, cyclohexadienyl, and the like.

The term "pharmaceutically acceptable salt" means a salt form of a compound with alkali metals such as sodium, potassium and lithium, with alkaline earth metals such as calcium and magnesium, with organic bases such as dicyclohexylamine, tributylamine, pyridine, and with amino acids such as arginine, lysine and the like. Compounds may also form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

The compounds of formula I may form salts which are also within the scope of this invention. Pharmaceutically acceptable (i.e., non-toxic, physiologically acceptable) salts are preferred, although other salts may also be used depending on the application, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

The term "alkyl" refers to saturated aliphatic groups including straight chain, branched chain, and cyclic groups, all of which may be optionally substituted.

The term "substituted alkyl" refers to an alkyl group substituted by, for example, one to four substituents, such as, halo, alkanoyl, aryloxy, alkanoyloxy, amino, alkylamino, substituted alkylamino, cycloalkylamino, substituted cycloalkylamino, arylamino, substituted arylamino, aralkylamino, methylene, methyl, ethyl, propyl and the like, and each of these moieties may also be optionally substituted.

The term "alkenyl" refers to unsaturated groups which contain at least one carbon-carbon double bond and includes straight chain, branched chain, and cyclic groups, all of which may be optionally substituted.

The term "substituted" refers to groups substituted by one to five substituents, independently selected from lower alkyl (acyclic or cyclic), aryl (carboaryl or heteroaryl) alkenyl, alkynyl, alkoxy, halo, haloalkyl (including trihaloalkyl, such as trifluoromethyl), mercapto, alkylthio, alkylsulfinyl, alkylsulfonyl, nitro, alkanoyl, alkanoyloxy, alkanoyloxyalkanoyl, alkoxycarboxy, aminocarbonyl, formyl, carboxyl, hydroxyl, cyano, azido, keto, and cyclic ketals thereof, alkanoylamido, heteroaryloxy, and heterocarbocyclicoxy.

The term "alkynyl" refers to straight or branched chain hydrocarbon groups, containing unit(s) of unsaturation [carbon-carbon triple bond(s)] from 2 to 20 carbon atoms, and most preferably 2 to 16 carbon atoms.

The term "substituted alkynyl" refers to an alkynyl group substituted by a substituent, examples include; halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "heteroatom" includes any atom other than hydrogen or carbon and can include, for example, oxygen, phosphorus, sulfur and nitrogen.

The terms "parenteral carrier system" (including variations thereof such as the various specific injectable and infusible dosage forms) refer to compositions comprising one or more pharmaceutically suitable excipients, such as solvents like water and co-solvents, solubilizing compounds, wetting compounds, suspending compounds, thickening compounds, emulsifying compounds, chelating compounds, buffers, pH adjusters, anti-oxidants, reducing compounds, anti-microbial preservatives, bulking compounds, protectants, tonicity adjusters and special additives.

The terms "therapeutically effective dose" (and variations thereof) refer to an amount, dose or dosing regimen of a compound (i.e., active pharmaceutical ingredient, prodrug or precursor thereof) that, upon interaction with a biological material, is sufficient to treat or prevent a disease state or undesirable conditions, whereby such dose may vary depending on the form of the compound, the biological material's condition and/or severity, the route of administration, the age of the biological material and the like.

A "chemotherapeutic agent" refers to a chemical compound which is released to treat or kill a tumor cell. Examples include: Abraxane, Adcetris, Adriamycin, Afinitor, Afinitor Disperz, Alimta, Alkeran, Alkeran, Aredia, Arimidex, Aromasin, Arranon, Arzerra, Avastin, Beleodaq, Bexxar, Blenoxane, Blincyto, Bosulif, Campath, Camptosar, Caprelsa, Casodex, Cerubidine, Clolar, Cometriq, Cosmegen, Cotellic, Cyramza, Cytoxan, Dacogen, Decadroo, DepoCyt, Dexpak Taperpak, Docefrez, Doxil, Droxia, Eligard, Elspar, Emcyt, Erbitux, Erivedge, Erwinaze, Ethyol, Etopophos, Eulexin, Fareston, Farydak, Faslodex, Femara, Firmagon, Fludara, Folex, Foloty, Gazyva, Gemzar, Gilotrif, Gleevec, Halaven, Herceptin, Hexalen, Hycamtin, Hydrea, Ibrance, Iclusig, Ifex, Imbruvica, Imiquimod, Inlyta, Iressa, Istodax, Ixempra, Jakafi, Jevtana, Kadcyla, Keytruda, Kyprolis, Lanvima, Leukeran, Leukine, Leustatin, Lonsurf, Lupron, Lynparza, Lysodren, Matulane, Megace, Mekinist, Mesnex, Metastron, Mexate, Mustargen, Mutamycin, Myleran, Mylotarg, Navelbine, Neulasta, Neupogen, Nexavar, Nilandron, Nipent, Nolvadex, Novantrone, Odomzo, Oncaspar, Oncovin, Ontak, Onxol, Opdivo, Panretin, Paraplatin, Perjeta, Platinol, Pomalyst, Proleukin, Purinethol, Reclast, Revlimid, Rheumatrex, Rituxan, Rubex, Sandostatin, Soltamox, Sprycel, and the like.

The terms "treating," "treatment," "treat" or "therapy" of a disease or disorder means slowing, stopping, or reversing progression of the disease or disorder, as evidenced by a reduction or elimination of either clinical or diagnostic symptoms, using the compositions and methods of the present invention as described herein.

The terms "preventing," or "prevention" of a disease or disorder means prevention of the occurrence or onset of a disease or disorder or some or all of its symptoms.

Additionally, it will be understood that any list of such candidates or alternatives is merely illustrative, not limiting, unless implicitly or explicitly understood or stated otherwise. As used in this specification and the appended claims, the singular forms "a", "an" and "the" include plural referents unless the content clearly dictates otherwise.

In some embodiments, the definition of terms used herein is according to International Union of Pure and Applied Chemistry (IUPAC) naming standards. Additionally, it will be understood that any list of such candidates or alternatives are merely illustrative, and not limiting, unless implicitly or explicitly understood or stated otherwise.

In addition, unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

The general usefulness of the disclosed invention lies in the selective drug delivery of immunomodulator to a specific location. The disclosed novel composition of matter allows for treatment and prevention options for a plurality of disease states and even provide provides a means of upregulating the immune response if a condition requires it.

The immune system is comprised of innate and acquired immunity, both of which work cooperatively to protect the host from microbial infections. It has been shown that innate immunity can recognize conserved pathogen-associated molecular patterns through Toll-Like Receptors (TLRs) expressed on the surface and interior of immune cells. Recognition of invading pathogens then triggers cytokine production and upregulation of co-stimulatory molecules on phagocytes, leading to modulation of T-cell function. Thus, innate immunity is closely linked to acquired immunity and can influence the development and regulation of an acquired response.

TLRs are a family of type I transmembrane receptors characterized by an $NH_2$-terminal leucine-rich repeat sensing domain (LRR) and a COOH-terminal intracellular tail containing a conserved signaling region based on the Toll/IL-1 receptor (TIR) homology domain. The LRR sensing domain contains a varying number of LRR, which are thought to be involved in ligand binding. Eleven TLRs have been described to date in humans and mice and they differ from each other in ligand specificities, expression patterns, and in the target genes they can induce.

Immunotherapeutics have been studied for their ability to leverage the body's own immune system to raise an immune response against established tumors. The immunostimulatory capacity of a variety of immunostimulants has been well documented. Depending upon their nature and composition and administration, immunostimulants are capable of inducing T-helper 1 (Th1) responses, or suppressing T-helper 2 (Th2) responses, and in some instances, inducing Th2 responses. As immunotherapeutics, the imidazoquinoline compounds exhibited β-galactosidase-directed immune cell activation or cytokine production (TNF, IL-6, IL-12).

In addition, certain imidazoquinolines have shown to be effective at eliciting an immune response that have been harnessed for the treatment of disease. With evidence showing that imidazoquinoline compounds may be used, for example, for the treatment of cholera, plague, typhoid, hepatitis B infection, influenza, inactivated polio, rabies, measles, mumps, rubella, polio, yellow fever, tetanus, diphtheria, haemophilus influenzae b, meningococcus infection, and pneumococcus infection. Imidazoquinoline compounds have also been shown to have anti-cell proliferative effective amount along with anti-cancer effects for the treatment of cancer for example basal skin cell carcinoma and melanoma.

However, one of the major obstacles for this class of immunotherapy is equal parts drug delivery and off-target activity. As such, direct intratumoral infusion is traditionally utilized, due to severe inflammatory toxicity that results from systemic routes of administration. The present embodiment demonstrates a novel composition of matter that allows for a means to overcome these challenges using a directed enzyme prodrug therapy approach.

One of the benefits of the several embodiments disclosed herein are based, on the observation that imidazoquinolines function as immunostimulants, but it should be noted that imidazoquinolines are only one embodiment of the disclosed invention. Imidazoquinolines are potent agonists for TLRs 7 and 8 present on innate immune cells, and activation of this set of TLRs on immune cells within the tumor microenvironment results in robust innate and adaptive anti-tumor immune responses. To date, imidazoquinolines have demonstrated clinical efficacy with precancerous lesions and basal skin cell carcinomas, with more modest success against melanomas. Although, administering imidazoquinolines via systemic routes leads to inflammatory toxicity, they have been used in-vitro to generate anti-tumor immune responses for cancers not amenable to direct intratumoral infusion by topical application. Taken together, these results imply that imidazoquinolines could become more broadly applicable cancer immunotherapeutics if non-specific inflammatory toxicity were better controlled by targeting activity to cancer cells. Thus, this could be accomplished by using imidazoquinolines in an enzyme-directed targeting strategy to confine immunostimulant effects to the tumor microenvironment.

In one aspect, the imidazoquinoline compounds, and analogs thereof used in the methods and compositions of the invention, are easy to administer. They have potential for finer specificity compared to existing immunostimulants, thus providing improved efficacy and safety profiles. Compounds and analogs thereof were attached via linkers, enzyme substrates and delivery systems to form a pharmaceutically relevant effect. In a preferred embodiment, a compound or enzyme will stimulate conversion of an enzyme-directed pro-immunostimulant to immunostimulant which can induce a cell-mediated immune response in the subject.

In one embodiment, the immunomodulator can be conjugated to an enzyme substrate via a linker. In embodiments involving linker, the linker can be conjugated to several enzyme substrates with such examples including pyranosides, furanosides, and mannosides. The enzyme substrates may be removed by endogenous enzymes, enzymes expressed by targeted transfection, or exogenous enzymes delivered by an anti-cancer antibody, an anti-viral antibody, an anti-bacterial antibody, an anti-fungal antibody, an anti-allergen antibody, or an anti-self antigen antibody.

Other embodiments provide the use of the compounds of the invention, in the manufacture of medicament for immune stimulation, and another agent, for simultaneous separate or sequential administration.

Specific Description

Synthesis of Imiquimod-β-Galactopyranoside

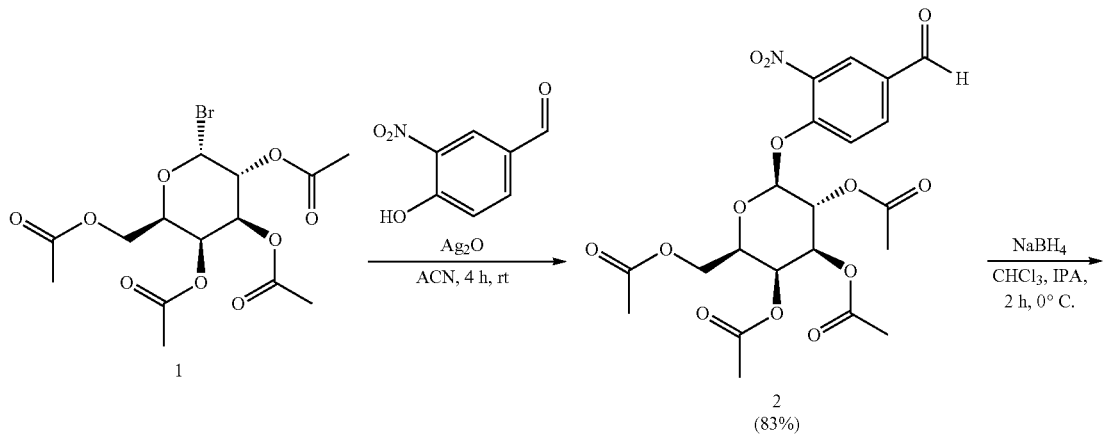

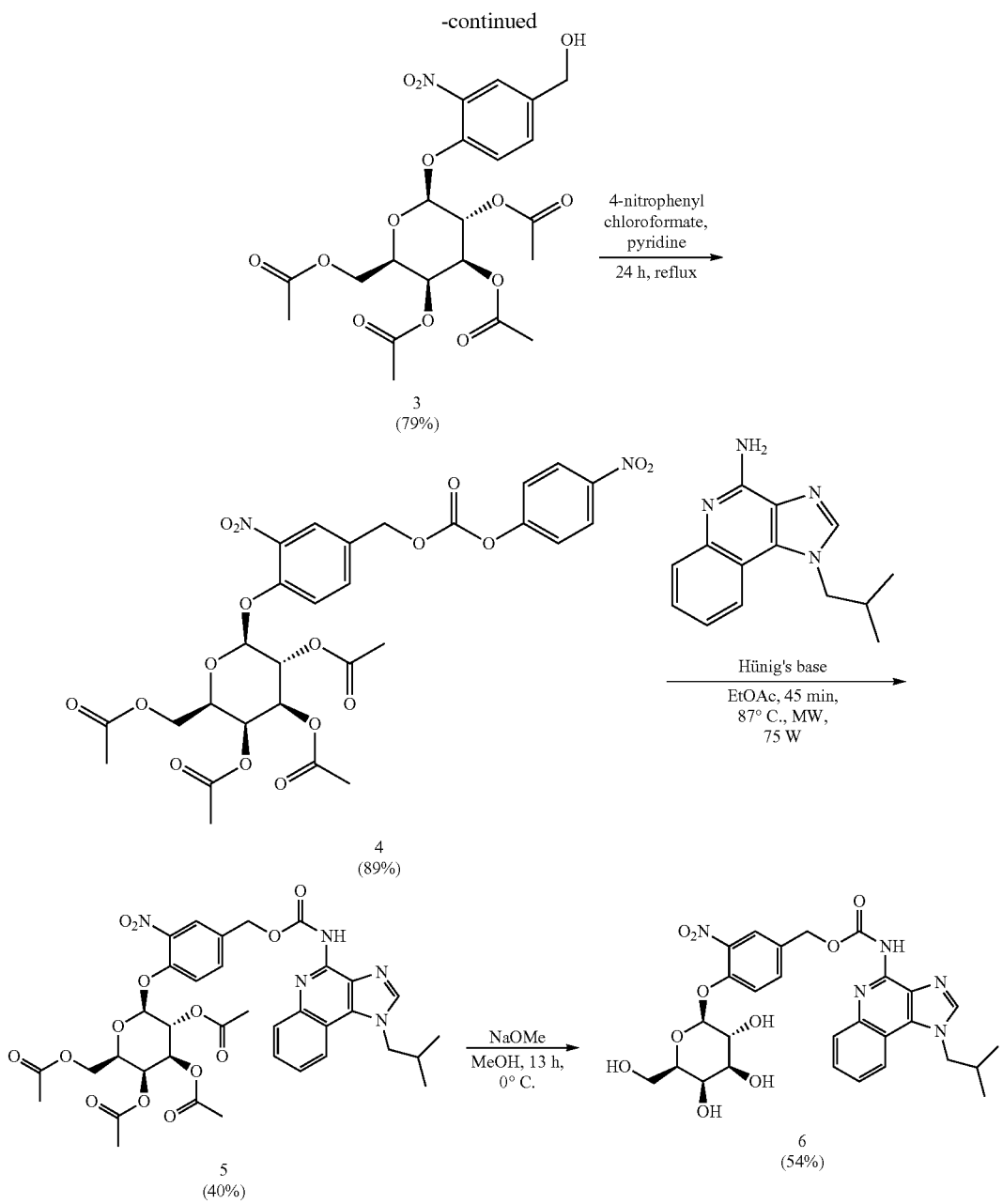

The starting material 1 was etherified with 3-nitro-4-hydroxybenzaldehyde under refluxing conditions with Ag$_2$O. The resulting aldehyde 2 was reduced with NaBH$_4$ to provide alcohol intermediate 3 prior to treatment with p-nitrophenyl chloroformate to arrive at 4 similar to literature procedure. Next, carbamoylation with Imiquimod was carried out under basic conditions to obtain 5. Further deprotection was carried out under standard Zemplén deacetylation conditions to obtain 6 in 13% linear yield over 5 steps.

The conceptual underpinning of the disclosed technology is what is known as a directed enzyme prodrug therapy (DEPT) approach to immunotherapeutic. This approach was evaluated and demonstrated by FIGS. 1a-b wherein the disclosed compound 6 was exposed to β-galactosidase. The exposure of 2 nmol of compound 6 before and after the addition of β-galactosidase (1 U) resulted in quantitative conversion into Imiquimod, showing that the basic mechanism of activation is functional and that an exemplary embodiment of the invention is capable of a selective controlled release. The FIGS. 1a-b also show the matching activity to that obtained with β-galactosidase-enriched B16 cells (5 mU) resulted in quantitative conversion of the compound over 3 h; in RAW-Blue cells, activity of compound alone (▲) is abrogated relative to the compound with 1 U β-galactosidase (♦) or the parent immunostimulant Imiquimod (■); *p<0.005 for the compound with β-galactosidase relative to blank.

With β-galactosidase-directed activation of RAW-Blue cells being demonstrated, the pro-immunostimulant was tested in the presence β-galactosidase-enriched B16 melanoma cells to show the subsequent activation of immune reporter cells via bystander effects. This not only proves that the compound can be selectively delivered to a target but also demonstrates the immunostimulant effect of the compound. FIGS. 2a-d show the in-culture activity of the compound with β-galactosidase-enriched B16 cells, where the conversion of compound 6 into Imiquimod was observed over 24 h with >36% conversion after 3 h. The addition of compound 6 to co-cultures of β-galactosidase-enriched B16 cells and RAW-Blue cells resulted in enhanced NF-κB transcription relative to co-cultures with unaltered B16 and RAW-Blue cells or RAW-Blue cells alone, showing that the compound does indeed activate an immune response. This result is further enforced by the experiments wherein the production of pro-inflammatory polarizing cytokines in JAWSII cells was also found to depend on β-galactosidase further enforcing both the mechanism of action and the controlled activation of the immune response.

Figure 3A:
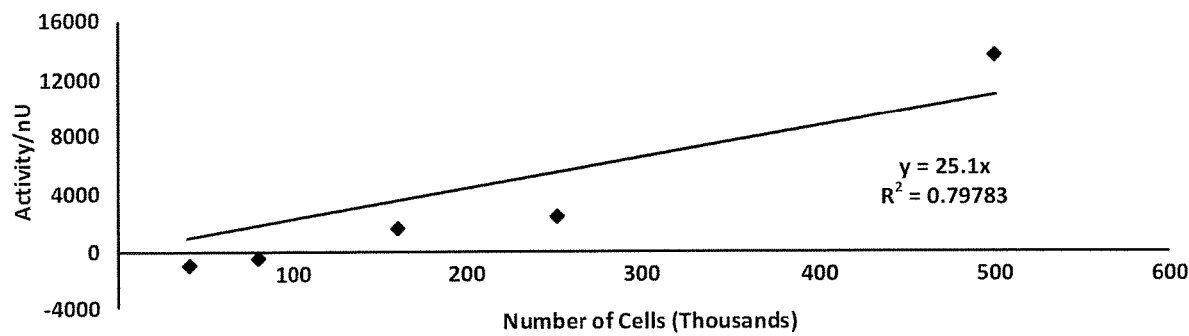
FIG. 3a shows the determination of β-galactosidase enzymatic activity (21.5 pU/cell) of β-gal-B16 melanoma cells. Cells where seeded in the indicated densities in 96 well plates and allowed to incubate with 4-nitrophenyl-β-galactopyranoside substrates (50 mM) for 2 hours before quantifying the percent conversion measured by absorbance at 405 nm.
Figure 3B:
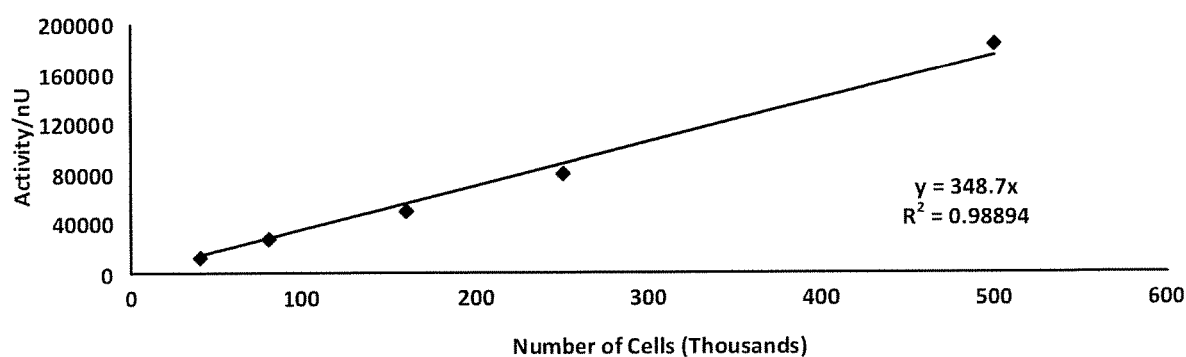
FIG. 3b shows the determination of β-galactosidase enzymatic activity (350 pU/cell) of β-gal-B16 melanoma cells. Cells where seeded in the indicated densities in 96 well plates and allowed to incubate with 4-nitrophenyl-β-galactopyranoside substrates (50 mM) for 2 hours before quantifying the percent conversion measured by absorbance at 405 nm.

Given the activation of the compound 6, the next step to show its viability as a treatment option for cancer would be to use the compound in an appropriate system. To that end, Murine B16-F10 melanoma cells were enriched with β-galactosidase through antibody-mediated biotinylation of glycoprotein 100 (gp 100), a tumor-associated antigen upregulated in the majority of melanomas. This was followed by treatment with avidin-β-galactosidase fusion protein, resulting in β-galactosidase-enriched B16 cells with an increase in β-galactosidase activity ranging from 20 to 350 pU per cell, or 2-35 mU per cell culture, as measured by conversion of 4-nitropenyl-β-galactopyramoside (NPG) as seen in FIGS. 3a-b.

Figure 4A:
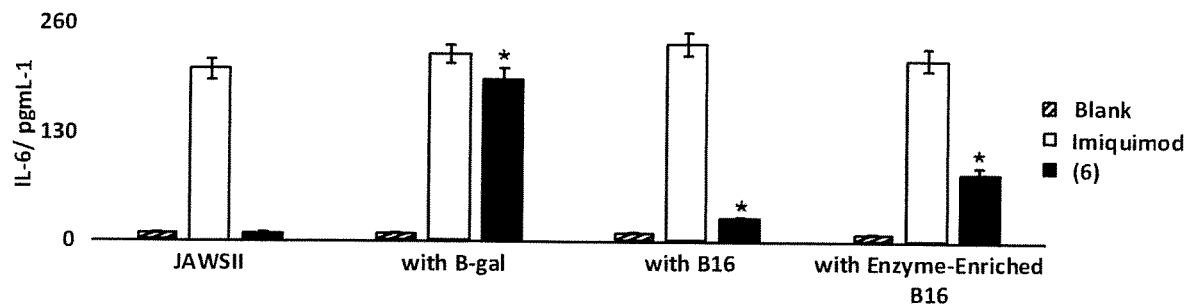
FIG. 4a shows the enzyme directed conversion of an immune-modulator to Imiquimod by soluble β-galactosidase in β-gal-B16 melanoma cells that was compared to JAWSII co-cultured alone or with cells containing the parent immunostimulant Imiquimod that were exposed to IL-6.
Figure 4B:
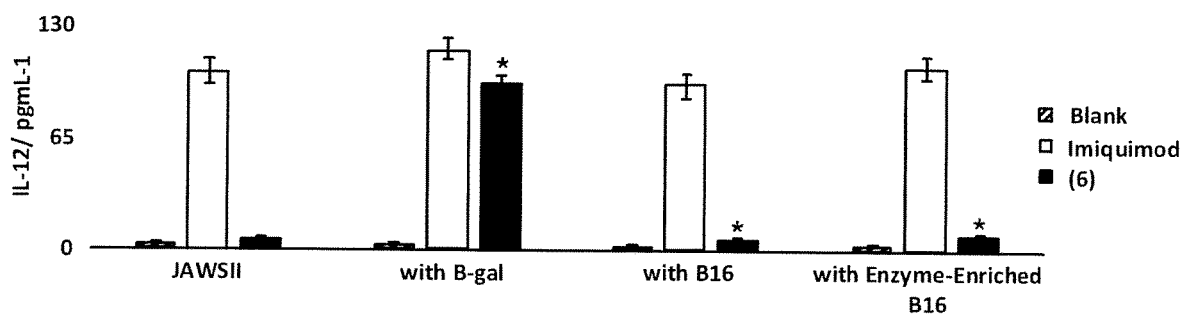
FIG. 4b shows the enzyme directed conversion of an immune-modulator to Imiquimod by soluble β-galactosidase in β-gal-B16 melanoma cells that was compared to JAWSII co-cultured alone or with cells containing the parent immunostimulant Imiquimod that were exposed to IL-12.
Figure 4C:
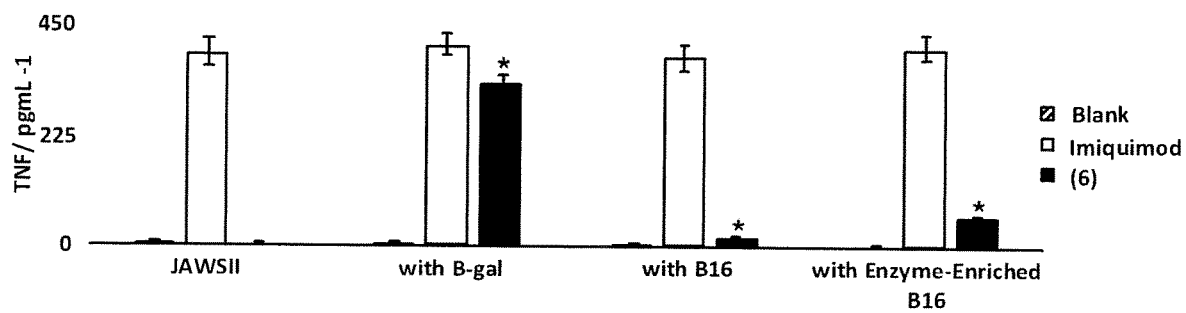
FIG. 4c shows the enzyme directed conversion of an immune-modulator to Imiquimod by soluble β-galactosidase in β-gal-B16 melanoma cells that was compared to JAWSII co-cultured alone or with cells containing the parent immunostimulant Imiquimod that were exposed to TNF.

To further demonstrate the immune response via cytokine production, the compound it was tested in the JAWSII murine monocyte cell line. This cell line was chosen because its activation by Imiquimod results in secretion of the pro-inflammatory cytokines tumor necrosis factor-α (TNF), IL-6, and IL-12, which are readily quantified by ELISA. JAWSII cell cultures where incubated with compound 6 at 5 μm to not induce significant pro-inflammatory cytokine production without β-galactosidase for any of the cytokines tested. JAWSII cell cultures that contained both compound 6 and exogenous β-galactosidase resulted in robust cytokine production that was similar to treatment with an equimolar concentration of Imiquimod. In this case, activation with compound 6 and exogenous β-galactosidase resulted in >80% of the cytokine production for all three cytokines tested relative to Imiquimod as shown by FIGS. 4a-c, confirming enzyme-directed conversion into bioavailable Imiquimod in vitro. Co-cultures of JAWSII and β-galactosidase-enriched B16 melanoma cells resulted in the production of pro-inflammatory cytokines when incubated with 6. These results indicate that compound 6 is converted into Imiquimod by β-galactosidase-enriched B16 cells before activating JAWSII cells via bystander effects, and the polarization of the immune response is comparable to Imiquimod as seen above. Marginally lower activity was observed in co-cultures containing β-galactosidase-enriched B16 cells relative to cultures containing soluble enzyme. This was speculated to be due to differences in enzymatic activity or spatial confinement of the enzyme on B16 cells, resulting in slower release over time and a lower acute dose of immunostimulant.

Figure 5:
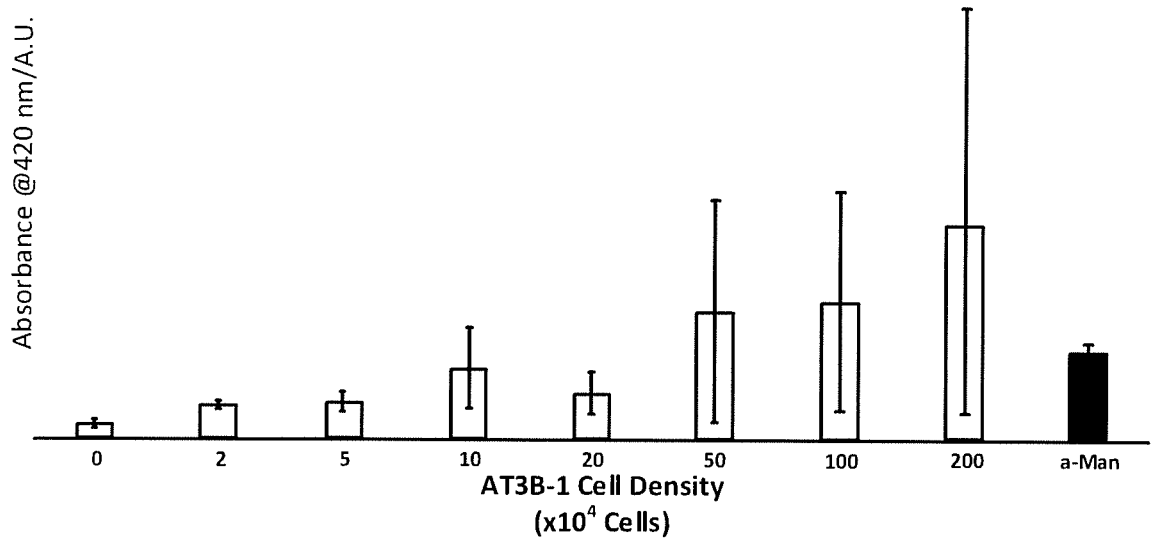
FIG. 5 show the varying densities of AT3B-1 cells treated with 10 mM of a pro-immunostimulant in dimethyl sulfoxide (DMSO).

To evaluate the disclosed compounds for their effect against multidrug-resistant cells and possible pathogen infection, compound 6 was exposed to a multidrug-resistant AT3B-1 prostate cancer cell line that is known to overexpress P-glycoprotein 1 (P-gp). AT3B-1 cells were plated in an optically clear bottomed 96-well plate at a range of densities (2–200×$10^4$ cells/well) in 180 μL of complete cell media. Each cell density was tested in triplicate with and without a 10 mM dose of compound 6. For wells with compound 6, 20 μL of a 100 mM stock solution of compound 6 in DMSO was used. As a control experiment, compound 6 was converted by exogenous α-Mannosidase (0.1 U/mL) in triplicate. The plate was incubated (37° C., 5% $CO_2$) for 72 h before measuring the absorbance at 420 nm. The average blank value (0.0725 A.U.) was used to normalize all absorbance values as seen in FIG. 5. The results of this experiment demonstrate that the compound is indeed interacting with P-gp.

Figure 6:
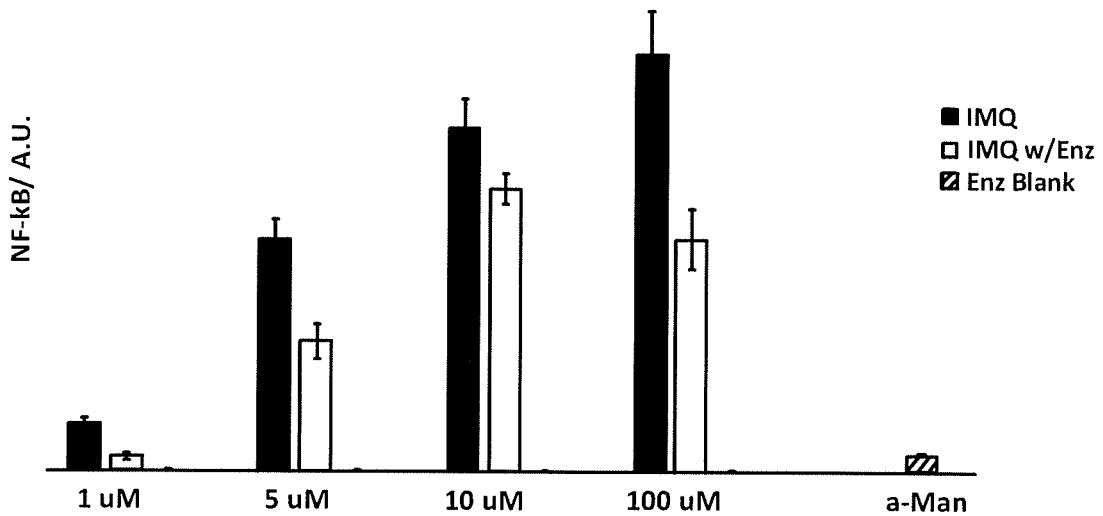
FIG. 6 show the RAW-Blue cells treated with varying concentrations of an immunostimulant.

To elucidate the interaction with P-gp, further studies with the AT3B-1 cell line were conducted to demonstrate that the activation of the compound was still occurring and having the desired effect of activating the immune response. To concretely determine the conversion of pro-immunostimulant (compound 6) to Imiquimod in the presence of α-Mannosidase over time for exogenous and endogenous experiments, 20 μL aliquots of 100 μM (pro-immunostimulant (compound 6)) in DMEM were incubated with 180 μL of either α-Mannosidase (0.1 U/mL, 37° C., 5% $CO_2$), or AT3B1 cells (1×105, or 5×105, or 1×106 cells, 37° C., 5% $CO_2$) without the addition of exogenous enzyme as shown by FIG. 6. To stop the reaction at the specified time points (0, 1, 2, 3, 6, 12, 24, and 48 h), 50 μL AO Quench Internal Standard (20 μg/mL, 2-methyl-4(3H)-quinazolinone in 1 M formic acid) was added to each individual reaction. Samples were then analyzed via LC-MS/MS. The substrate was detected using multiple reaction monitoring mode by monitoring the m/z fragmentation from 597.80 to 241.20 Da for compound 6 and the Imiquimod product was monitored for 241.20 to 185.10 Da fragmentation, showing that the compound was still being converted in the presence of enzyme and effluxed via interaction with P-gp or other cell surface transporter proteins, allowing for the use of the disclosed compound in both cancer and multidrug-resistant cancers that result from an overexpression of P-gp.

Figure 7:
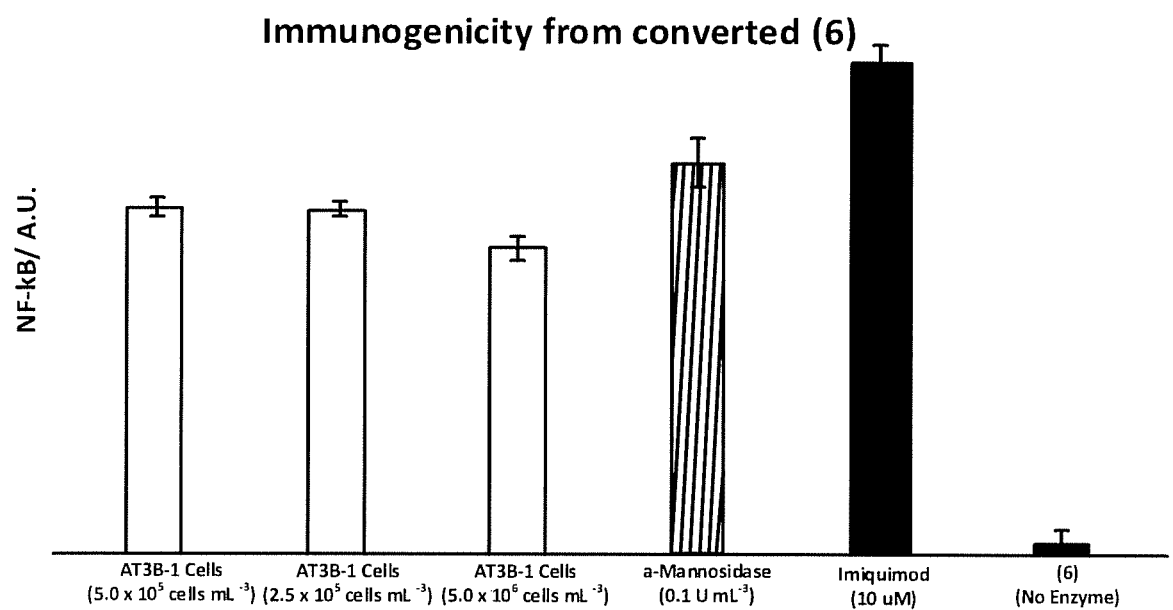
FIG. 7 shows the results of an inverse RAW-Blue assay, where RAW-Blue cells were treated with an immunostimulant generated in the presence of AT3B-1 prostate cancer cells.

To further demonstrate the utility of the compound in the presence of P-gp, inverse RAW-Blue assays were run to demonstrate that exogenous α-Mannosidase and AT3B-1 driven conversion of 10 μM Imiquimod-Mannopyranoside to Imiquimod confers immunogenicity. A range of AT3B-1 cell densities were tested and showed the activation of the compound in the presence of the P-gp rich cell lines. As a positive control, 10 μM doses of the TLR7 agonist Imiquimod were used. Imiquimod-Mannopyranoside was also examined without a conversion driver demonstrated abrogated activity as shown by FIG. 7. This further demonstrates that while the compound is being effected by P-gp the activation of the compound is still maintained along with the subsequent immune response needed for treating the disease state. This allows for the compounds of this invention to be utilized in the treatment of: cancer, multidrug-resistant cancer, multidrug-resistant pathogen infection, or comparable disease state resulting from under-activation of the immune system; asthma, Crohn's disease, or comparable disease state resulting from over-activation of the immune system.

EXAMPLES

Materials and Methods:

All solvents were reagent grade. Reactions were magnetically stirred and monitored by thin layer chromatography (TLC) with 0.25 mm pre-coated silica gel plates. Flash chromatography was performed with silica gel 60 (particle size 0.040-0.062 mm). Yields refer to chromatographically and spectroscopically pure compounds, unless otherwise stated. Proton and Carbon-13, HSQC and COSY NMR spectra were recorded on a 400 MHz spectrometer equipped with Agilent 7600 autosampler; one probe, 2-channel multi-tunable probe with auto-tuning and z-axis pulse field gradients.

Microwave reactions were carried out using a Biotage Initiator SP Wave microwave reactor with cooling air. Mass spectra were obtained using a Sciex4800 MALDI TOF/TOF analyzer with α-cyano-4-hydroxy-cinnamic acid CHCA matrix as a 10 mg/mL solution (1:1 0.1% TFA(aq):acetonitrile) used in a 1:1 ratio with sample solution. ATR-IR spectra (4000-650 $cm^{-1}$) were obtained using a Nicolet iS10 infrared spectrophotometer. Final purification was performed on a Dionex UltiMate 3000 HPLC (Thermo Scientific) equipped with a $C_{18}$ column at a flow rate of 1.5 mL/min, and UV detection at 254 nm. Cells were cultured in a Forma Scientific $CO_2$ water jacketed incubator (model 3110, 37° C., 5% $CO_2$). All cell centrifugation steps were performed at 200 RCF at 0° C. from 10 min on a Thermo Scientific Sorvall ST 16R centrifuge. Absorbance values for enzymatic assays (Raw-Blue and Nitrophenyl mannoside) were obtained on a Labtech FLUOstart Omega plate reader at 620 or 405 nm respectively. Conversion of Imiquimod-α-mannopyranoside to Imiquimod was measured by LC-MS/MS on a LC-20AD series HPLC system (Shimadzu, Columbia, Md.) fitted with a HTC PAL autosampler (LEAP technologies, Carroboro, N.C.). Chromatography for LC-MS/MS was performed Luna reverse-phase column (50×2.0 mm, 5 μm). Detection of Imiquimod-mannopyranoside and Imiquimod was conducted using an API 4000 Q-Trap tandem mass spectrometry system manufactured by Applied Biosystems/MDS Sciex using turbospray ESI operating in positive ion mode.

Chemical Synthesis

Chemical shifts are reported relative to chloroform (δ7.24) for or dimethyl sulfoxide (δ77.23) for 1H NMR and 13 C NMR. Absorption spectra were recorded on a 300 UV/VIS spectrophotometer using a 1 cm quartz cell. Fluorescence excitation and emission spectra were measured on Cary Eclipse fluorescence spectrophotometer.

Synthesis of Enzyme Substrate

Synthesis of 1-(4-formyl-2-nitrophenyl)peracyl-β-galactopyranoside: 1-(4-formyl-2-nitrophenyl)peracyl-β-galactopyranoside was synthesized according to a previously published procedure. Acetobromo-α-D-galactose (1.4 g, 3.5 mmol, 1.0 eq) and silver oxide (4.1 g, 18 mmol, 5.1 eq) were dissolved in 12 mL acetonitrile. Next, 4-hydroxy-3-nitrobenzaldehyde (0.60 g, 3.6 mmol, 1.0 eq) was suspended in 12 mL acetonitrile and added to the reaction mixture. The reaction was stirred for 4 h at room temperature under argon atmosphere. The crude reaction mixture was evaporated to dryness in vacuo and purified via column chromatography (0% to 1% MeOH in DCM over 6 CVs, 1% isocratic for 3 CVs, 1% to 3% MeOH over 14 CVs). Solvent was evaporated from the isolated product in vacuo to yield compound 2 as a white solid (1.4 g, 2.9 mmol, 83% yield); Rf (5% MeOH/DCM)=0.65; 1H NMR (400 MHz, [D3]Chloroform, 25° C.): δ=9.95 (s, 1H), 8.27 (d, J (H,H)=1.8 Hz, 1H), 8.05 (dd, J(H,H)=8.8, 2.0 Hz, 1H), 7.48 (d, J(H,H)=8.4, 1H), 5.55 (dd, J(H,H)=10.4, 8.4 Hz, 1H), 5.47 (d, J(H,H)=3.2 Hz, 1H), 5.21 (d, J(H,H)=8.0 Hz, 1H), 5.11 (dd, J(H,H)=10.4, 3.6 Hz, 1H), 4.27-4.20 (m, 1H), 4.18-4.14 (m, 2H), 2.16 (s, 3H), 2.09 (s, 3H), 2.05 (s, 3H), 1.99 (s, 3H) ppm; 13C (100 MHz, [D3]Chloroform, 25° C.): δ=188.7, 170.3, 170.16, 170.13, 169.2, 153.5, 141.2, 134.1, 131.4, 126.9, 118.7, 100.0, 71.9, 70.4, 67.6, 66.7, 61.4, 20.73, 20.68, 20.65, 20.62 ppm; IR (ATR): ν=2981, 2890, 1748, 1712.5, 1701, 1614, 1537, 1368, 1242, 1130, 1071, 1043 cm-1; UV/Vis (methanol): λ max(ε)=284. MS m/z calculated for C21H23NO13Na [M+Na]+520.10671; Observed 520.10931 Da.

Synthesis of Linker

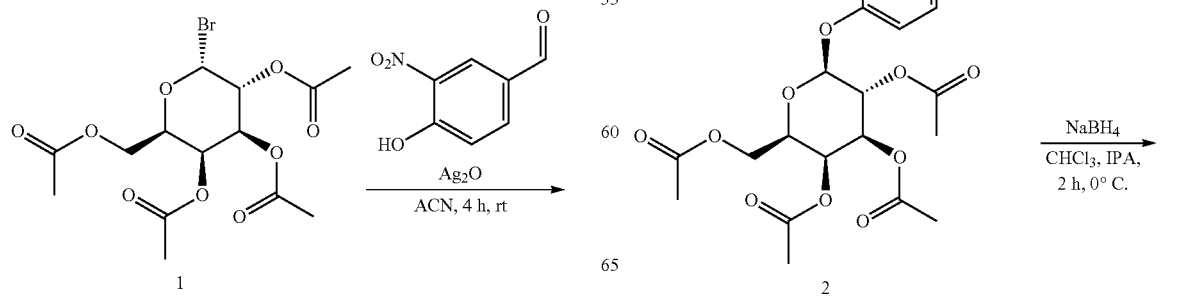

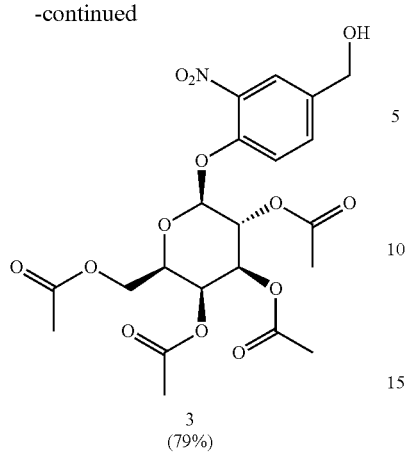

3
(79%)

Synthesis of 1-(4-hydroxymethyl-2-nitrophenyl)peracyl-β-galactopyranoside: 1-(4-hydroxymethyl-2-nitrophenyl)peracyl-β-galactopyranoside is synthesized according to a previously published procedure. The starting material 2 (1.4 g, 2.9 mmol, 1.0 eq) was dissolved in 16 mL CHCl3 and 6 mL 2-propanol in a flame-dried flask cooled on ice. Next, NaBH4 (0.54 g, 14 mmol, 5.0 eq) was added to the reaction mixture and stirred for 2 h under argon. The crude reaction was diluted with 75 mL CHCl3, washed 5 times with 100 mL water, dried over MgSO4, and solvent evaporated in vacuo to yield the product as a white solid (1.1 g, 2.3 mmol, 79% yield); Rf (75% EtOAc/Hexanes)=0.50; 1H NMR (400 MHz, [D3]Chloroform, 25° C.): δ=7.78 (d, J(H,H)=2.0 Hz, 1H), 7.50 (dd, J(H,H)=8.8, 2.0 Hz, 1H), 7.33 (d, J(H,H)=8.7 Hz, 1H), 5.51 (dd, J(H,H)=10.5, 8.0 Hz, 1H), 5.45 (d, J(H,H)=3.3 Hz, 1H), 5.09 (dd, J(H,H)=10.4, 3.2 Hz, 1H), 5.04 (d, J(H,H)=8.0 Hz, 1H), 4.70 (s, 2H), 4.24 (dd, J(H,H)=12.0, 7.2 Hz, 1H), 4.15 (dd, J(H,H)=11.6, 6.0 Hz, 1H), 4.06 (t, J(H,H)=6.7 Hz, 1H), 2.17 (s, 3H), 2.11 (s, 3H), 2.05 (s, 3H), 1.99 (s, 3H) ppm. 13C (100 MHz, [D3]Chloroform, 25° C.): δ=170.5, 170.32, 170.26, 169.6, 148.5, 141.4, 137.3, 131.9, 123.3, 120.1, 101.0, 71.5, 70.7, 68.0, 66.9, 63.6, 61.5, 20.79, 20.77, 20.69 ppm; IR(ATR) ν=3580, 3462, 2964, 2938, 2890, 1745, 1624, 1532, 1499, 1370, 1354, 1271, 1229, 1072, 1045 cm-1; UV/Vis (methanol): λmax(ε)=307 nm. MS m/z calculated for C21H25NO13Na [M+Na]+522.1224; Observed 522.1229 Da.

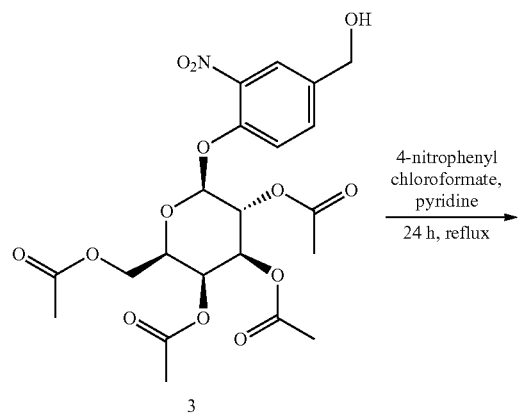

3

→ 4-nitrophenyl chloroformate, pyridine
24 h, reflux

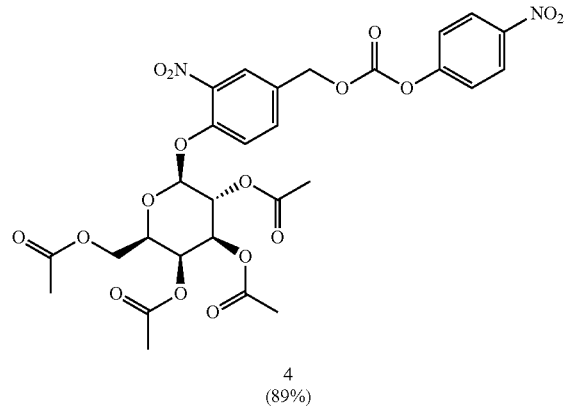

4
(89%)

Synthesis of 2-nitro-4-((((nitrophenoxy)carbonyl)oxy)methyl)phenoxy)-peracyl galactopyranoside: 2-nitro-4-((((nitrophenoxy)carbonyl)oxy)methyl)phenoxy)-peracyl galactopyranoside was synthesized according to a previously published procedure. Compound 3 (0.12 g, 0.25 mmol, 1.0 eq) and 4-nitrophenyl chloroformate (0.12 g, 0.58 mmol, 2.3 eq) were dissolved in 10 mL dry DCM in a flame-dried flask. Pyridine (50 µL, 0.62 mmol, 2.5 eq) was added and the reaction was heated to reflux for 1 day under argon. Reaction was diluted with 50 mL water, and extracted 3 times with 10 mL DCM. Organic layers were collected, washed 3 times with 50 mL water, dried over MgSO4, and solvent evaporated in vacuo. The crude reaction mixture was separated using column chromatography (12% EtOAc for 1 CV, 12% to 40% over 8 CVs, 40% for 8 CVs, 40% to 100% over 8 CVs, 100% for 6 CVs). Solvent was evaporated to yield compound 4 as a translucent solid (0.146 g, 0.22 mmol, 89% yield); Rf (60% EtOAc/Hexanes)=0.64; 1H NMR (400 MHz, [D6]DMSO, 25° C.): δ=8.32 (d, J(H,H)=9.2 Hz, 2H), 8.04 (s, 1H), 7.83 (d, J(H,H)=8.7 Hz, 1H), 7.58 (d, J(H,H)=9.2 Hz, 2H), 5.63 (d, J(H,H)=7.2 Hz, 1H), 5.38 (d, J(H,H)=3.1 Hz, 1H), 5.33 (s, 2H), 5.31-5.27 (m, 1H), 5.27-5.22 (m, 1H), 4.50 (t, J(H,H)=6.3 Hz, 1H), 4.17-4.11 (m, 2H), 2.15 (s, 3H), 2.04 (s, 6H), 1.95 (s, 3H) ppm; 13C (100 MHz, [D6]DMSO 25° C.): δ=169.92, 169.85, 169.5, 168.9, 155.2, 151.8, 148.4, 145.2, 140.1, 134.3, 130.1, 125.4, 124.9, 122.6, 117.8, 98.5, 70.8, 69.9, 68.6, 67.7, 67.1, 61.2, 20.50, 20.38, 20.32, 20.30 ppm. IR(ATR): ν=2971, 1750, 1620, 1538, 1368, 1218, 1166, 1073 cm-1; UV/Vis (methanol): λmax(ε)=286 nm. MS m/z calculated for C28H28N2O17Na [M+Na]+687.12857; Observed 687.12915 Da.

Synthesis of Immunostimulant

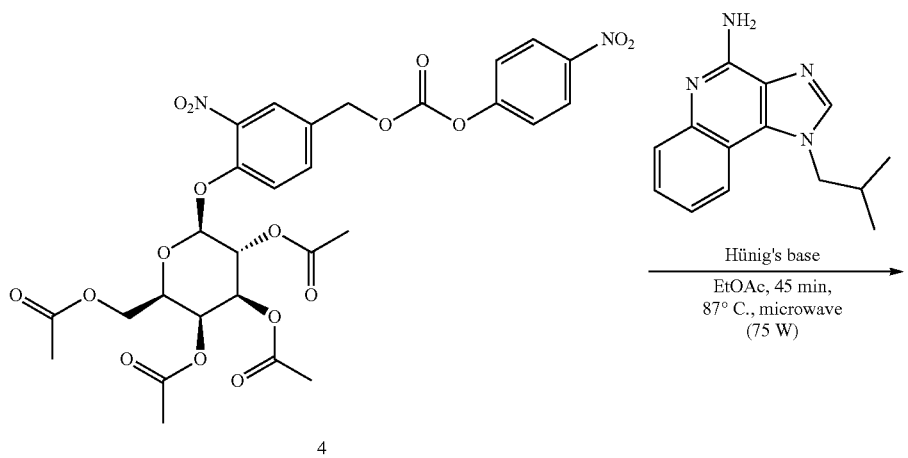

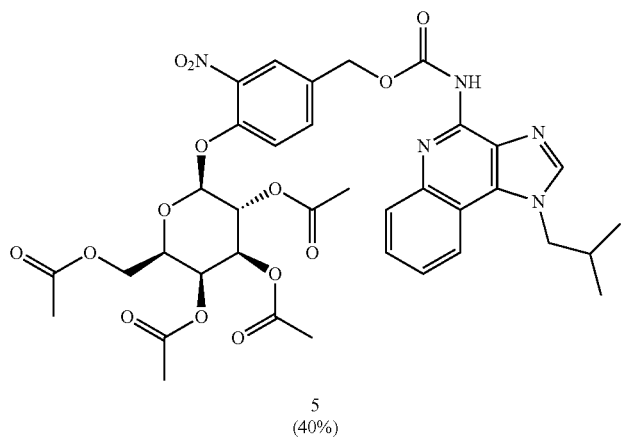

Synthesis of 4-Imiquimod-2-nitrophenyl-peracyl galactopyranoside: Imiquimod (90 mg, 0.33 mmol, 1.9 eq) and Hünig's base (0.075 mL, 0.43 mmol, 2.5 eq) were dissolved in 2 mL of EtOAc that was dried overnight prior to use. The mixture was stirred for 20 min in a microwave reaction vessel before addition of compound 4 (0.11 g, 0.17 mmol, 1.0 eq) dissolved in 2 mL of dry EtOAc. The reaction was placed in a Biotage Initiator+ microwave reactor (87° C., 75 W average) and irradiated for 45 min. Solvent was evaporated from the resulting crude reaction mixture in vacuo before purification via column chromatography (1% MeOH in DCM for 20 CVs, 1% to 10% over 10 CVs). Product fractions were collected, solvent evaporated, and lyophilized from benzene to yield compound 5 as a white powder (52 mg, 0.07 mmol, 40% yield); Rf (100% EtOAc)=0.40; 1H NMR (400 MHz, [D6]DMSO, 25° C.): δ=10.10 (s, 1H), 8.35 (s, 1H), 8.24 (d, J(H,H)=8.0 Hz, 1H), 8.04 (s, 1H), 7.96 (d, J(H,H)=8.0 Hz, 1H), 7.80 (d, J(H,H)=8.4 Hz, 1H), 7.66 (t, J(H,H)=7.6 Hz, 1H), 7.61 (t, J(H,H)=6.8 Hz, 1H), 7.43 (d, J(H,H)=10.8 Hz, 1H), 5.60 (d, J(H,H)=6.8 Hz, 1H), 5.36 (d, J(H,H)=3.0 Hz, 1H), 5.30-5.22 (m, 4H), 4.51-4.47 (m, 3H), 4.18-4.10 (m, 2H), 2.22-2.17 (m, 1H), 2.04 (s, 3H), 2.03 (s, 3H), 2.02 (s, 3H), 1.95 (s, 3H), 0.92 (d, J=6.4, 6H) ppm; 13C (100 MHz, [D6]DMSO, 25° C.): δ=169.9, 169.8, 169.5, 168.9, 152.7, 147.8, 144.7, 144.4, 142.9, 140.2, 133.4, 133.2, 132.4, 131.1, 128.9, 127.3, 125.4, 123.7, 120.8, 117.7, 116.7, 98.6, 70.8, 69.9, 67.7, 67.1, 64.3, 61.2, 53.5, 28.4, 20.49, 20.38, 20.32, 20.30, 19.3 ppm. IR(ATR): ν=2963, 1750, 1601, 1582, 1534, 1480, 1371, 1235, 1073 cm-1; UV/Vis (methanol): λ max(ε)=284 nm. MS m/z calculated for C36H40N5O14 [M+H]+766.25718; Observed 766.25488 Da.

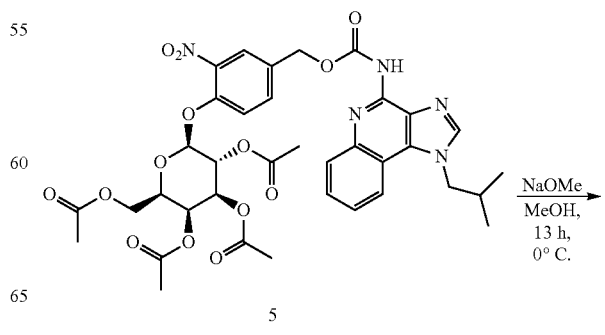

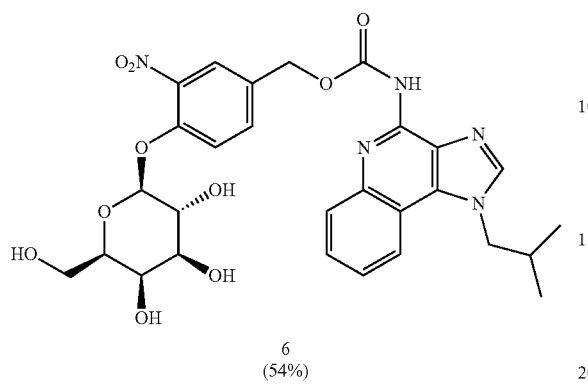

6
(54%)

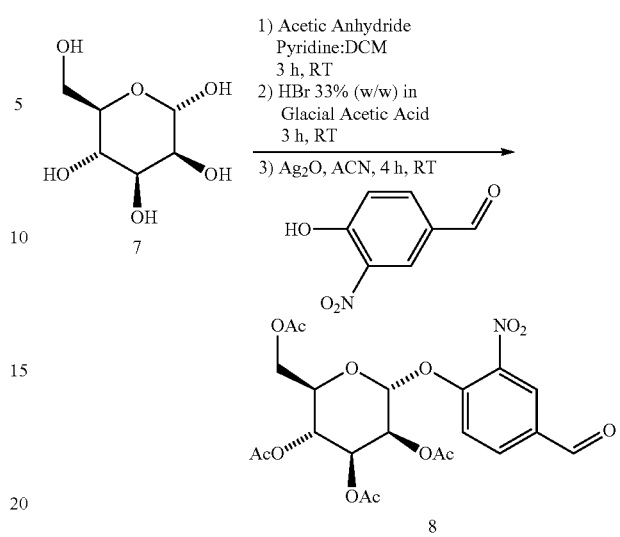

Synthesis of 2,3,4,6-tetraacetyl-1-bromo-mannopyranoside

Synthesis of 4-Imiquimod-2-nitrophenyl-galactopyranoside: Compound 5 (0.14 g, 0.18 mmol, 1.0 eq) was dissolved in 5 mL dry MeOH in a flame-dried flask cooled on ice. Next, a 0.05 M NaOMe solution was prepared by diluting 1 mL of 0.5 M NaOMe in 9 mL of dry MeOH. The methanolic NaOMe solution (0.36 mL, 18 µmol, 0.10 eq) was added dropwise over 10 min, and the reaction was stirred for 13 h under argon. The reaction was neutralized with DOWEX 50WX8 ion exchange resin, filtered with a 0.2 µm syringe filter, and evaporated to dryness in vacuo. The crude reaction mixture was isolated via column chromatography (7% MeOH in DCM for 17 CVs, 7% to 15% for 5 CVs, 15% for 18 CVs) to yield Imiquimod-β-galactopyranoside (6) (58 mg, 0.10 mmol, 54% yield); Rf (10% MeOH:DCM) 0.29. Aliquots of (6) were further purified via HPLC, using a mobile phase composed of 35% MeOH in water for 10 min, 35% to 90% over 5 min, 90% for 10 min, 35% for 5 min, with an elution time of 19.258 min at a flow rate of 1.0 mL/min. Both MeOH and water contained 0.1% TFA. Purity of purified (6) was estimated to be >98% by HPLC. 1H NMR (400 MHz, [D6]DMSO, 25° C.): δ=10.07 (s, 1H), 8.35 (s, 1H), 8.25 (d, J(H,H)=7.9 Hz, 1H), 8.00-7.95 (m, 2H), 7.72 (dd, J(H,H)=8.8, 2.0, 1H), 7.67 (t, J(H,H)=7.2, 1H), 7.61 (t, J(H,H)=7.2 1H), 7.45 (d, J(H,H)=8.8 Hz, 1H), 5.21 (s, 2H), 5.17 (d, J(H,H)=5.2 Hz, 1H), 5.05 (d, J(H,H)=7.5 Hz, 1H), 4.90 (d, J(H,H)=9.0 Hz, 1H), 4.68 (t, J(H,H)=4.8 Hz, 1H), 4.61 (d, J(H,H)=4.4 Hz, 1H), 4.49 (d, J(H,H)=7.2 Hz, 2H), 3.70 (t, J(H,H)=3.6 Hz, 1H), 3.63 (t, J(H,H)=6.4 Hz, 1H), 3.57-3.46 (m, 2H), 3.45-3.38 (m, 1H), 2.24-2.14 (m, 1H), 0.93 (d, J(H,H)=6.5 Hz, 6H) ppm; 13C (100 MHz, [D6]DMSO 25° C.): δ=152.7, 149.1, 144.7, 144.4, 143.0, 139.9, 133.4, 133.3, 131.1, 130.5, 128.9, 127.3, 125.4, 123.8, 120.8, 117.1, 116.7, 101.1, 75.8, 73.4, 70.0, 68.0, 64.5, 60.3, 53.5, 28.4, 19.3 ppm. IR(ATR): ν=3355, 3000, 2961, 2324, 2164, 2033, 1747, 1602, 1531, 1206, 1062, 1069, 1072.8 cm-1; UV/Vis (methanol): λ max(ε)=286 nm. MS m/z calculated for C28H32N5O10 [M+H]+598.21492; Observed 598.21381 Da.

The compound was synthesized by adapting two previously published procedures. To a flame-dried 250 mL round-bottom flask with stir bar was added D-(+)-Mannose (7) (1.0 g, 5.6 mmol, 1.0 eq) under argon atmosphere. (7) was then suspended in anhydrous pyridine (12 mL) and anhydrous methylene chloride (14 mL). Acetic anhydride (32 mL, 330 mmol, 12 eq/hydroxyl) was added dropwise over 17 minutes through an addition funnel. After 3 h, solvent was removed in vacuo through toluene azeotrope (3×75 mL), resulting in a yellow colored oil. The oil was dissolved in methylene chloride (26 mL) and the addition funnel was then charged with hydrogen bromide (33% w/w) in glacial acetic acid (32 mL, 130 mmol, 24 eq). The reaction flask was equilibrated in a 0° C. ice bath before the solution was added dropwise. After addition, the mixture was warmed to room temperature and stirred for an additional 3 h. At this point, the reaction flask was submerged in a 0° C. ice bath and the addition funnel loaded with DI water (21 mL). The reaction was quenched via dropwise addition of water with the flask inside the ice bath. The solution was then washed with chilled 10% NaHCO3 (3×50 mL) and a final wash with brine (1×50 mL). The organic layer was dried over MgSO4 and solvent was removed in vacuo, resulting in a translucent oil. The oil was dissolved in anhydrous acetonitrile (26 mL) and transferred to a 100 mL round-bottom flask with stir bar. Next, 4-hydroxy-3-nitrobenzaldehyde (0.93 g, 5.5 mmol, 1.0 eq) was added, followed by silver oxide (7.7 g, 33 mmol, 6.0 eq). The mixture was stirred under argon atmosphere at room temperature for 4 h. At this point, the solution was diluted with methylene chloride (40 mL) and the slurry was filtered through a layer of activated charcoal on top of a layer of Celite® and rinsed with more methylene chloride (80 mL). Solvent was removed from the filtrate in vacuo and a crude yellow oil was obtained. The crude product was separated using flash chromatography with an 80 g silica gel column (Gradient, 0% MeOH 2 column volumes (CVs), 0% to 5% MeOH in DCM over 6 CVs, 5% MeOH isocratic over 6 CVs) The desired fractions were combined and solvent removed in-vacuo to obtain a yellow oil. The oil was lyophilized from 40% ACN in water to obtain (8) as a yellow-white powder (0.75 g, 1.5 mmol, 27% yield). $^1$H NMR (400 MHz, DMSO-d6, 25° C.): δ=9.99 (s, 1H; HCO), 8.53 (d, j(H,H)=2.0 Hz, 1H; ArCH), 8.23 (dd, J(H,H)=8.8, 2.4 Hz, 1H; ArCH), 7.72 (d, j(H,H)=8.8 Hz, 1H; ArCH), 6.21 (d, j(H,H)=2.0 Hz, 1H; CH), 5.41 (dd, j(H,H)=3.6, 2.0 Hz, 1H; CH), 5.33 (dd, J(H,H)=10, 3.6 Hz, 1H; CH), 5.23 (t, J(H,H)=10 Hz, 1H; CH), 4.16 (dd, J(H,H)=12, 5.6 Hz, 1H; CH$_2$), 4.05 (qd, J(H,H)=9.9, 5.3, 2.0 Hz, 1H; CH), 3.95 (dd, J(H,H)=12, 2.4 Hz, 1H; CH$_2$), 2.17 (s, 3H; CH$_3$), 2.05 (s, 3H; CH$_3$), 1.98 (s, 3H; CH$_3$), 1.91 (s, 3H; CH$_3$) ppm; $^{13}$C NMR (100 MHz, DMSO-d6, 25° C.) δ=190.57, 169.79, 169.50, 169.46, 169.38, 151.51, 139.87, 134.62, 130.54, 127.02, 117.82, 95.30, 69.66, 68.12, 67.66, 64.68, 61.43, 20.54, 20.43, 20.39, 20.37 ppm; UV/VIS (Methanol): $\lambda_{Max}$(ε)=250 nm (18000); IR (ATR): ν=2959, 1740, 1698, 1611, 1578, 1537, 1496, 1366, 1214, 1162, 1137, 1051, 971 cm$^{-1}$; HRMS (Expected for [C$_{21}$H$_{23}$NO$_{13}$+Na]$^+$: 520.1067, Observed 520.1065 (Δ=0.5 ppm), Expected for [C$_{21}$H$_{23}$NO$_{13}$+K]$^+$: 536.0906, Observed 536.08173 (Δ=2.1 ppm))

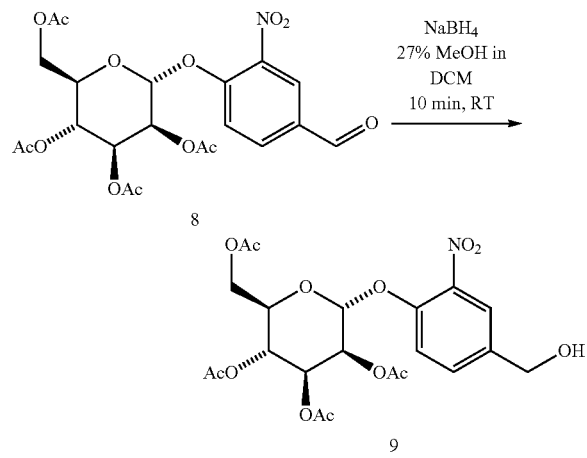

Synthetic procedures for subsequent compounds closely follow our synthetic procedures for synthesis of an Imiquimod Galactopyranoside. To a flame-dried 50 mL pear-shaped flask with stir bar was added compound (8) (0.67 g, 1.3 mmol, 1.0 eq) dissolved in anhydrous 27% methanol in methylene chloride (10 mL). The solution stirred for several minutes before adding sodium borohydride (0.26 g, 6.7 mmol, 5.0 eq) to the flask in one portion. The mixture was stirred for 10 min before quenching with DI water (20 mL). The aqueous layer was extracted with methylene chloride (3×10 mL). The combined organic layers were dried over MgSO$_4$ and solvent removed to give a yellow residue. The crude residue was lyophilized from benzene to acquire (9) (0.547 g, 1.10 mmol, 82% yield) as a pale yellow solid. $^1$H NMR (400 MHz, DMSO-d6, 25° C.) δ=7.90 (d, J(H,H)=2.0 Hz, 1H; ArCH), 7.63 (dd, J(H,H)=8.8, 2.4 Hz, 1H; ArCH), 7.48 (d, J(H,H)=8.4 Hz, 1H; ArCH), 5.99 (d, J(H,H)=2.0 Hz, 1H; ArCH), 5.42, (t, J(H,H)=6.4 Hz, 1H; OH), 5.38 (d, J(H,H)=1.6 Hz, 1H; CH), 5.32 (dd, J(H,H)=10, 3.4 Hz, 1H; CH), 5.21 (t, J(H,H)=10 Hz, 1H; CH), 4.52 (d, J(H,H)=5.6 Hz, 2H; CH$_2$), 4.15 (dd, J(H,H)=12, 5.4 Hz, 1H; CH$_2$), 4.08-4.04 (m, 1H), 3.97 (dd, J(H,H)=12, 2.4 Hz, 1H; CH$_2$), 2.16 (s, 3H; CH$_3$), 2.05 (s, 3H; CH$_3$), 1.97 (s, 3H; CH$_3$), 1.92 (s, 3H; CH$_3$) ppm; $^{13}$C NMR (100 MHz, DMSO-d6, 25° C.) δ=169.80, 169.51, 169.51, 169.44, 146.08, 139.71, 137.93, 132.32, 122.91, 117.76, 95.46, 69.42, 68.24, 67.90, 64.87, 61.54, 61.32, 20.57, 20.44, 20.40, 20.38 ppm; UV/VIS (Methanol): $\lambda_{max}$(ε)=227 nm (7200); IR (ATR): ν=3318, 2961, 1750, 1732, 1621, 1528, 1500, 1369, 1215, 1170, 1143, 1047, 1022 cm$^{-1}$; HRMS (Expected for [C$_{21}$H$_{25}$NO$_{13}$+Na]$^+$: 522.1224, Observed 522.12091, (Δ=2.9 ppm), Expected for [C$_{21}$H$_{25}$NO$_{13}$+K]$^+$: 538.0963, Observed 538.09486, (Δ=2.7 ppm))

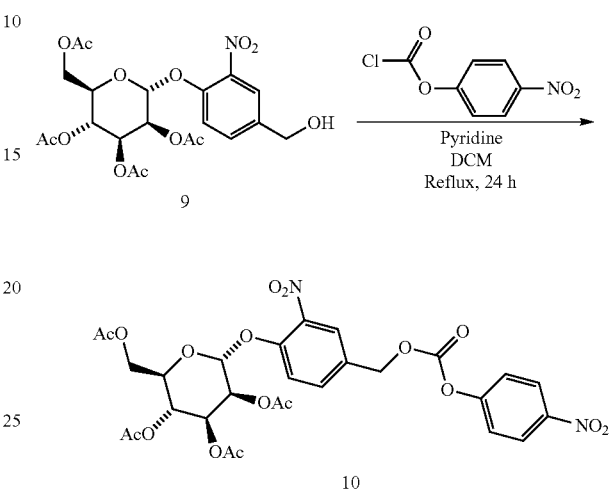

To a flame-dried 100 mL round-bottom flask was added compound (9) (0.262 g, 0.525 mmol, 1.0 eq) dissolved in anhydrous methylene chloride (21 mL). Next, 4-nitrophenyl chloroformate (0.241 g, 1.20 mmol, 2.3 eq) and anhydrous pyridine (105 µL, 1.30 mmol, 2.5 eq) were added to the round-bottom flask. The solution was lowered into a pre-heated 90° C. oil bath and refluxed for 24 hours, at which point the reaction was quenched by the addition of DI water (50 mL). The aqueous layer was extracted with methylene chloride (3×20 mL) and the combined organic layers were washed with DI water (3×40 mL). Organics were dried over MgSO$_4$ and solvent was removed in vacuo to yield a crude oil. The oil was then dissolved in hot methylene chloride (3 mL) and precipitated by addition of room temperature 40% ethyl acetate in hexanes (10 mL). Crystals were collected and dried to recover (10) as a white solid (0.208 g, 0.313 mmol, 60% yield). $^1$H NMR (400 MHz, DMSO-d6, 25° C.): δ=8.32 (dd, J(H,H)=7.0, 2.2 Hz, 2H; ArCH), 8.14 (d, J(H,H)=2.4 Hz, 1H; ArCH), 7.83 (dd, J(H,H)=8.8, 2.4 Hz, 1H), 7.60-7.56 (m, 3H; ArCH), 6.08 (d, J(H,H)=1.6 Hz, 1H; CH), 5.40 (dd, J(H,H)=3.6, 2.0 Hz, 1H; CH), 5.35 (s, 2H; CH$_2$), 5.32 (d, J(H,H)=3.6 Hz, 1H; CH), 5.22 (t, J(H,H)=10 Hz, 1H; CH), 4.16 (dd, J(H,H)=12, 5.6 Hz, 1H; CH$_2$), 4.08-4.04 (m, 1H; CH), 3.98 (dd, J(H,H)=12, 2.2 Hz, 1H; CH$_2$), 2.17 (s, 3H; CH$_3$), 2.05 (s, 3H; CH$_3$), 1.98 (s, 3H; CH$_3$), 1.91 (s, 3H; CH$_3$) ppm; $^{13}$C NMR (100 MHz, DMSO-d6, 25° C.): δ=169.79, 169.52, 169.50, 169.42, 155.21, 151.78, 147.48, 145.21, 139.62, 134.75, 129.68, 125.70, 125.42, 122.56, 117.90, 95.30, 69.50, 68.63, 68.20, 67.84, 64.82, 61.52, 20.56, 20.44, 20.40, 20.36 ppm; UV/VIS (Acetonitrile): $\lambda_{Max}$(ε)=263 nm (7000); IR (ATR): ν=3092, 2962, 1742, 1617, 1595, 1526, 1494, 1377, 1349, 1266, 1212, 1166, 1139, 1006, 859 cm$^{-1}$; HRMS (Expected for [C$_{28}$H$_{28}$N$_2$O$_{17}$+Na]$^+$: 687.1286 Observed 687.1271, (Δ=2.8 ppm), Expected for [C$_{28}$H$_{28}$N$_2$O$_{17}$+K]$^+$: 703.1025 Observed 703.10388, (Δ=2.0 ppm))

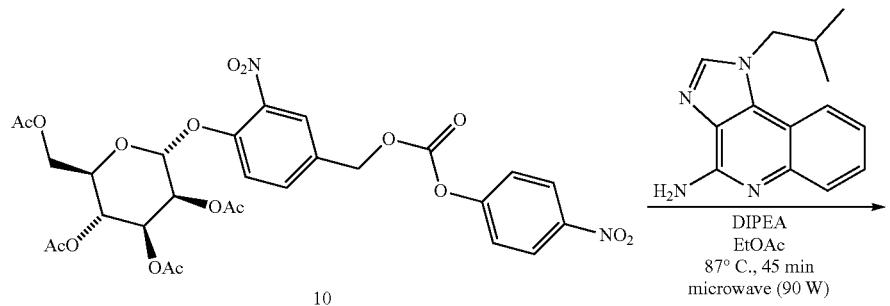

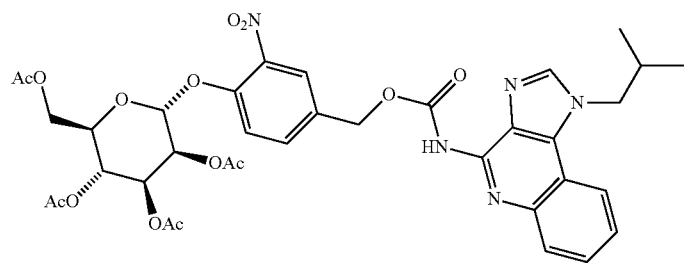

11

To a 5 mL microwave reactor vial with stir vane was added compound (10) (0.15 g, 0.23 mmol, 1.0 eq) dissolved in dry ethyl acetate (6 mL). Next, Imiquimod (0.10 g, 0.42 mmol, 1.9 eq) and Hünig's base (98 µL, 0.56 mmol, 2.5 eq) were added to the vial. The vial was sealed, placed in a microwave reactor and irradiated for 45 min (87° C., 90 W, pre-stirring: 30 s). After the solution had cooled to room temperature, the insoluble material was filtered off and the filtrate concentrated in vacuo. The crude material was submitted to flash chromatography (isocratic, 100% EtOAc, rf=0.96) and the desired fractions were collected, solvent evaporated, and the material lyophilized from benzene to obtain compound (11) (0.032 g, 0.042 mmol, 19% yield) as a white solid. $^1$H NMR (400 MHz, DMSO-d6, 25° C.): δ=10.09 (s, 1H; CONH), 8.35 (s, 1H; ArCH), 8.21 (d, J(H,H)=8.0 Hz, 1H; ArCH), 8.13 (d, J(H,H)=2.0 Hz, 1H; ArCH), 7.97 (d, J(H,H)=8.0 Hz, 1H; ArCH), 7.81 (dd, J(H,H)=8.6, 2.0 Hz, 1H; ArCH), 7.68-7.54 (m, 3H; ArCH), 6.05 (d, J(H,H)=1.2 Hz, 1H; CH), 5.39 (dd, J(H,H)=3.4, 1.8 Hz, 1H; CH), 5.33 (dd, J(H,H)=10, 3.4 Hz, 1H; CH), 5.24-5.19 (m, 3H; CH$_2$, CH), 4.49 (d, J(H,H)=7.6 Hz, 2H; CH$_2$), 4.15 (dd, J(H,H)=12, 5.4 Hz, 1H; CH$_2$), 4.06 (qd, J(H,H)=9.8, 5.4, 2.0 Hz, 1H; CH), 3.97 (dd, J(H,H)=12, 2.0 Hz, 1H), 2.23-2.16 (m, 4H; CH, CH$_3$), 2.05 (s, 3H; CH$_3$), 1.97 (s, 3H; CH$_3$), 1.89 (s, 3H; CH$_3$), 0.92 (d, J(H,H)=6.8 Hz, 6H; (CH$_3$)$_2$); $^{13}$C NMR (100 MHz, DMSO-d6, 25° C.) δ=169.80, 169.51, 169.50, 169.42, 152.65, 146.82, 144.71, 144.34, 142.94, 139.70, 133.70, 133.37, 131.93, 131.13, 128.86, 127.34, 125.34, 124.53, 120.79, 117.77, 116.70, 95.31, 69.47, 68.22, 67.86, 64.81, 64.34, 61.51, 53.50, 28.42, 20.56, 20.44, 20.40, 20.36, 19.29 ppm; UV/VIS (Methanol): λ$_{Max}$(ε)=246 nm (71000); IR (ATR): ν=2962, 1746, 1581, 1531, 1477, 1427, 1367, 1213, 1132, 1055, 972, 759 cm$^{-1}$; HRMS (Expected for [C$_{36}$H$_{38}$N$_4$O$_{15}$+Na]$^+$: 766.2572, Observed 766.25757, (Δ=0.5 ppm))

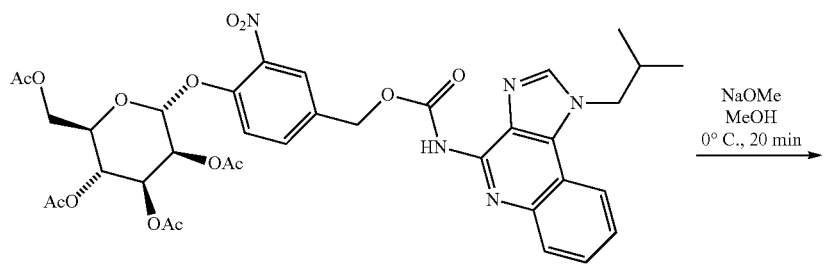

11

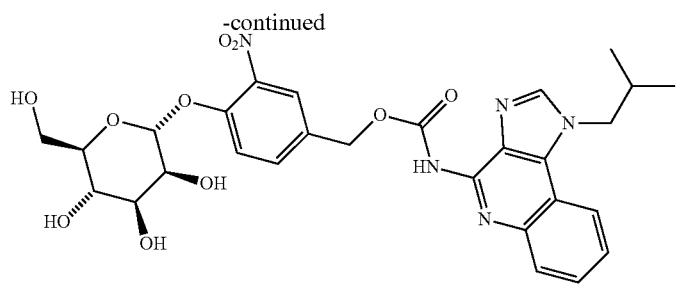

12

Synthesis of 2-nitro-4-((((Imiquimod)carbonyl)oxy) methyl)phenoxy) Mannopyranoside: Compound (12) was synthesized by modifying a previously published procedure for galactose. To the scintillation vial containing compound (11) (0.018 g, 0.023 mmol, 1 eq) was added a stir bar and anhydrous methanol (635 µL). Next, a freshly prepared solution of 0.05 M sodium methoxide in methanol (980 µL, 0.049 mmol, 2 eq) was added turning the solution yellow. After 20 mins TLC showed no remaining starting material and a scoop of Dowex 50WX8(H) was added and left to stir for 10 mins. At which point the solution was colorless. Organics were filtered through a 5 µm syringe filter and solvent was removed under reduced pressure. Crude material was purified by reverse phase prep HPLC using a gradient method. The fractions were collected and lyophilized from water to obtain compound (12) (0.0027 g, 0.004 mmol, 17% yield) as a white solid. 1H NMR (400 MHz, DMSO-d6, 25° C.) δ=8.29 (dd, J(H,H)=7, 2 Hz, 2H), 8.11 (d, J(H,H)=4 Hz, 1H), 7.80 (dd, J(H,H)=8, 2 Hz, 1H), 7.57-7.52 (m, 3H), 6.05 (d, J(H,H)=2 Hz, 1H), 5.37 (dd, J(H,H)=4, 2 Hz, 1H), 5.32 (s, 2H), 5.20 (d, J(H,H)=4 Hz, 1H), 5.19 (t, J(H,H)=8 Hz, 1H), 4.12 (dd, J(H,H)=12, 8 Hz, 1H), 4.06-4.00 (m, 1H), 3.95 (dd, J(H,H)=12, 4 Hz, 1H), 2.14 (s, 3H), 2.02 (s, 3H), 1.94 (s, 3H), 1.88 (s, 3H) ppm; $^{13}$C NMR (100 MHz, DMSO-d6, 25° C.): δ=170.22, 169.95, 169.93, 169.86, 155.64, 152.21, 147.91, 145.64, 140.06, 135.18, 130.10, 126.13, 125.85, 122.99, 118.33, 96.73, 69.93, 69.06, 68.63, 68.27, 65.25, 61.96, 20.99, 20.87, 20.83, 20.79 ppm; UV/VIS (Methanol): λmax(ε)=223 nm; IR (ATR): ν=3092, 2962, 1742, 1617, 1595, 1526, 1494, 1377, 1349, 1266, 1212, 1166, 1139, 1006, 859 cm$^{-1}$; HRMS (Expected for $[C_{28}H_{30}N_4O_{11}+H]^+$: 598.2149, Observed 598.21649, (Δ=2.7 ppm), Expected for $[C_{28}H_{30}N_4O_{11}+Na]^+$: 620.1969, Observed 620.19861, (Δ=2. ppm)).

Imiquimod-δ-Galactopyranoside Conversion to Imiquimod by LC-MS/MS

For LC-MS/MS experiments, mobile phase A consisted of 0.05% formic acid and 0.2% acetic acid in water, and mobile phase B comprised 90% acetonitrile, 9.9% water, and 0.1% formic acid. Using a flow rate of 400 µL/min, mobile phase B 5% isocratic for 0.5 min, before gradient to 95% B over 2.2 min, followed by 95% isocratic for 0.1 min. The total chromatographic assay time (including time to equilibrate for the next run) was 4.0 min per sample. Optimized mass spectrometer parameters were as follows: collision gas, 20 psig; curtain gas, 20 psig; ion source gas 1, 60 psig; ion source gas 2, 40 psig; ion spray voltage, 5500 V; desolvation temperature, 600° C.; declustering potential, 70 V; entrance potential, 10 V; collision energy, 50 V; collision cell exit potential, 10 V. The substrate was detected using multiple reaction monitoring mode by monitoring the m/z fragmentation from 597.8 to 241.2 Da for (6) and the Imiquimod product was monitored for 241.2 to 185.1 Da fragmentation.

Figure 1B:
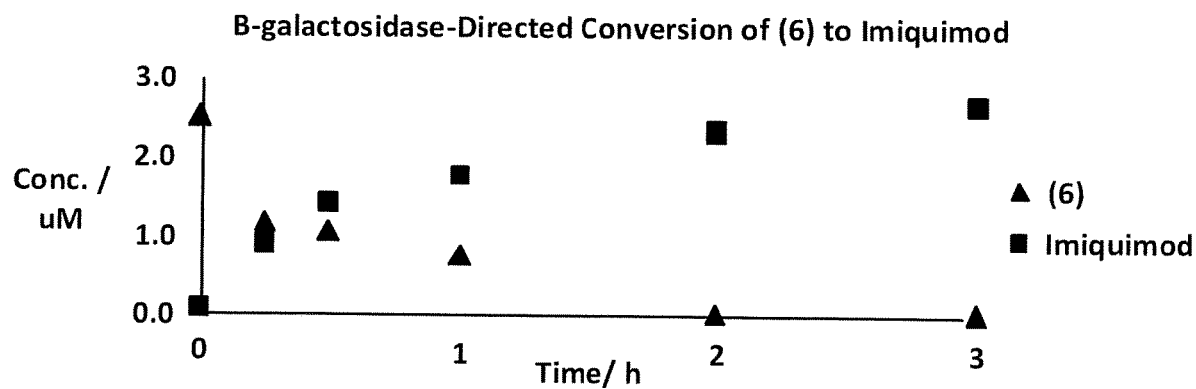
FIG. 1b shows the matching activity that was obtained with β-galactosidase-enriched B16 cells resulting in quantitative conversion of an immune-modulator.
Figure 1C:
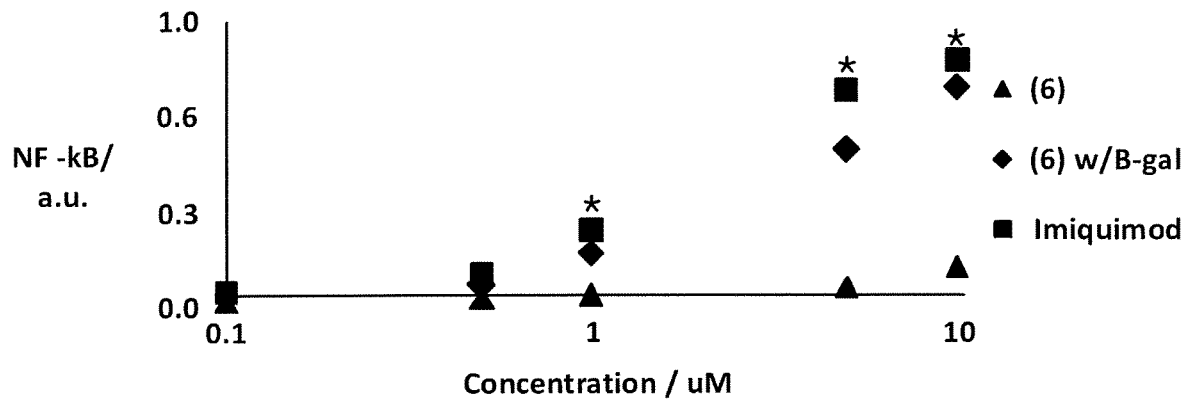
FIG. 1c shows RAW-Blue cell activity of an immune-modulator separated relative to 1 U β-galactosidase or the parent immunostimulant Imiquimod.
Figure 2A:
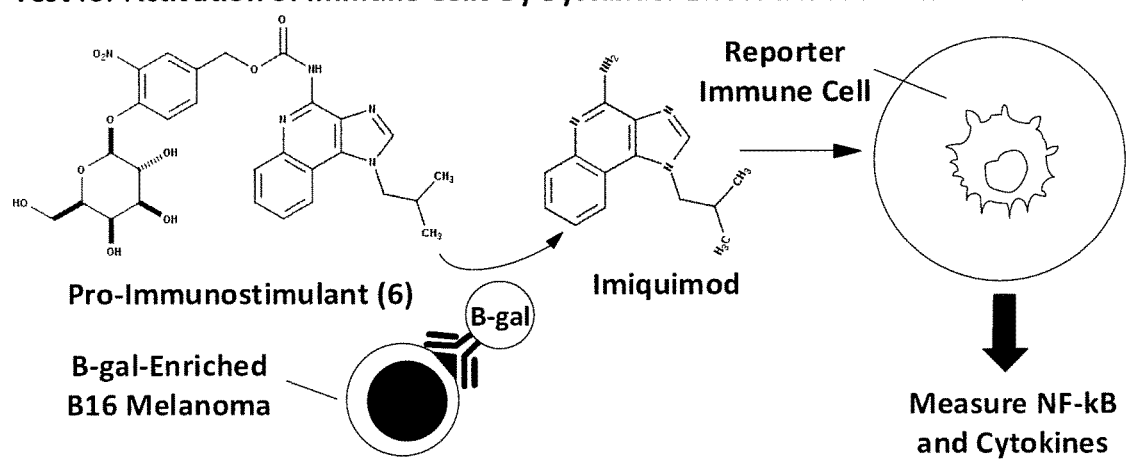
FIG. 2a shows the conversion of an immune-modulator into Imiquimod by utilizing β-galactosidase-enriched B16 melanoma cells.
Figure 2B:
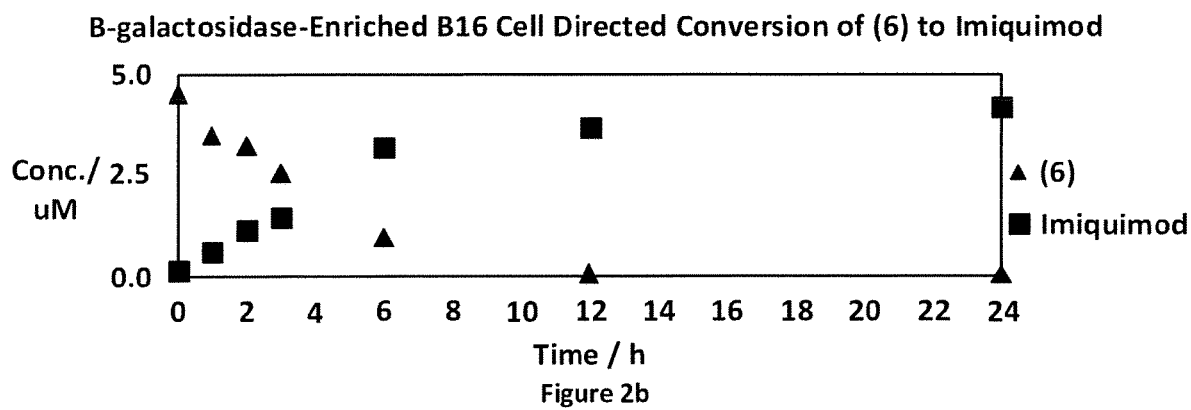
FIG. 2b shows the conversion of an immune-modulator using β-galactosidase-enriched B16 cells resulted in >36% conversion after 3 h, and quantitative conversion after 24 h.
Figure 2C:
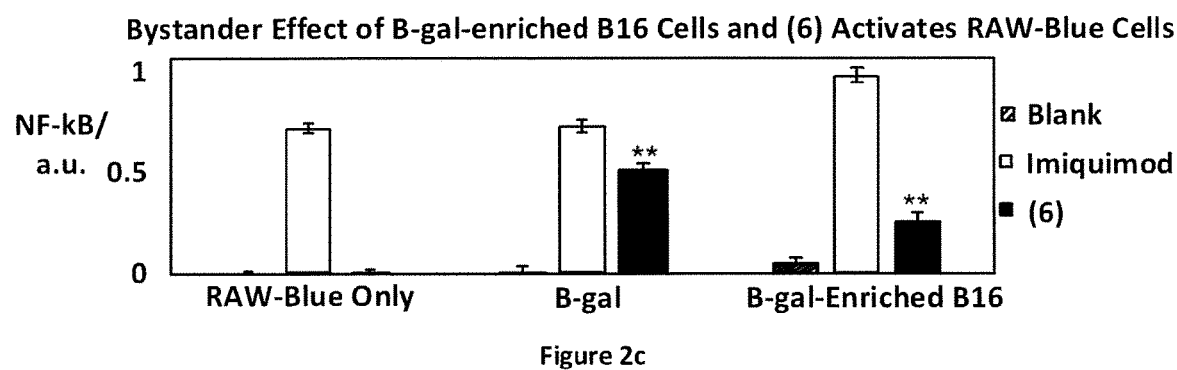
FIG. 2c shows the activation of RAW-Blue cells by an immunomodultor that was dependent on β-galactosidase added as a soluble enzyme or that was depending on β-galactosidase-enriched B16 melanoma cells.
Figure 2D:
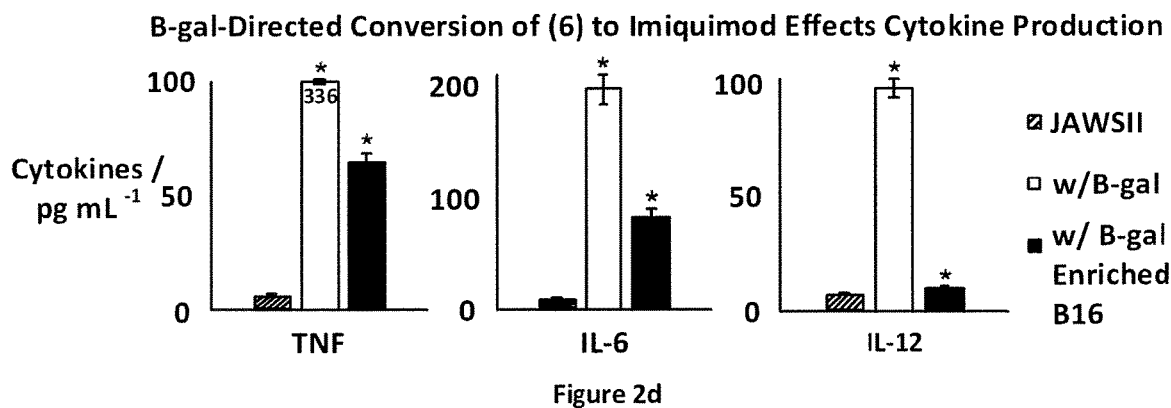
FIG. 2d shows the production of pro-inflammatory polarizing cytokines in JAWSII cells that was found to depend on β-galactosidase.

To confirm the chemical identity of Imiquimod liberated by β-gal-mediated conversion of (6), an end-point assay was performed using 1 U of β-gal in 200 µL of 10 µm (6) incubated for 16 h (37° C., 5% $CO_2$). To stop the reaction, 50 µL AO Quench Internal Standard (20 µg/mL 2-methyl-4(3H)-quinazolinone in 1 m formic acid) was added to the reaction. This aliquot was compared to a 200 µL sample of 10 µm (6) without β-gal enzyme. Samples of (6) without enzyme resulted in an LC peak at 1.68 min with m/z=597.8 and 241.2 Da corresponding to (6); no residual Imiquimod was observed indicating that (6) was stable to these conditions. Compound (6) incubated with β-gal enzyme resulted in a single peak at 1.57 min with m/z=241.2 and 185.1 Da corresponding to Imiquimod with no residual (6) signal detected. This indicated quantitative conversion to Imiquimod had occurred as seen in FIGS. 1a-b.

To determine the conversion of Imiquimod-β-Galactopyranoside (6) to Imiquimod in the presence of β-gal over time for exogenous experiments, aliquots (200 µL) of (6) at a concentration of 5 µm in DPBS were incubated with β-gal (1 U, 37° C., 5% $CO_2$). To stop the reaction at the specified time points (0, 1, 2 min), 50 µL AO Quench Internal Standard (20 µg/mL 2-methyl-4(3H)-quinazolinone in 1 m formic acid) was added to each individual reaction. Depletion of (6) was measured by LC-MS/MS for each time point. Due to the rapid depletion of (6), it was decided that 1 U of enzyme could be used to liberate the immunostimulant in vitro. However, to better gauge the release of immunostimulant from (6) at enzyme activities comparable to enzyme enriched cells, a lower enzyme activity of 5 mU was also tested. Similar to above, aliquots of (6) for various time points (0, 0.25, 0.5, 1, 2, 3 h) were tested for conversion to immunostimulant by exogenous β-galactosidase. Depletion of (6) and formation of Imiquimod were measured by LC-MS/MS for each time point resulting in near quantitative conversion over 3 h.

To determine the conversion of Imiquimod-β-Galactopyranoside (6) to Imiquimod in the presence of β-galactosidase enzyme enriched B16 cells over time (see β-galactosidase-enrichment protocol below), aliquots of (6) over various time points (0, 1, 2, 3, 6, 12, 24 h) were tested for the conversion to immunostimulant in 96 well plates at a density of 1×105 cells/well and exhibited in an activity of 350 pU/cell, or 35 mU/well (Figure S3). Depletion of (6) and formation of Imiquimod were measured by LC-MS/MS for each time point resulting in near quantitative conversion over 24 h.

RAW-Blue Macrophages

As per manufacturer instructions, RAW-Blue cells (modified RAW264.7 macrophages) were grown in complete culture media composed of Dulbecco's Modified Eagle's Medium DMEM with 4.5 g/L glucose, 2 mM L-glutamine, 10,000 U/mL penstrep, and Zeocin (0.1 mg/mL) supplemented with 10% heat inactivated fetal bovine serum (HI-FBS). Media was changed every 3-4 days, and cells were passaged once per week. Passaging involved changing media, counting, and seeding $3\times10^5$ cells in 35 mL of new complete media in a new T-175 culture flask.

JAWSII Dendritic Cells

Immature murine bone marrow dendritic cells (JAWSII, Invivogen, Calif.) were grown in complete culture media composed of α-Modified Eagle Media (α-MEM, ThermoFisher, Mass.), supplemented with 5 ng/mL Granulocyte Macrophage Colony-Stimulating Factor (GM-CSF, PeproTech, Inc., N.J.), and 20% HI-FBS. Cells were passaged every 7-8 days. Passaging involved changing media, counting, and seeding $3\times10^5$ cells in 35 mL of new complete media in a new T-175 culture flask.

B16 Melanoma Cells

Murine melanoma cells (B16-F10, ATCC, Va.) were cultured in complete media composed of DMEM with 4.5 g/L glucose, 4.5 g/L L-glutamine, 10,000 U/mL penstrep, supplemented with 10% HI-FBS. Media was changed every 3-4 days, and cells were passaged once per week. Passaging involved changing media, removing adherent cells with trypsin-EDTA by incubating with enzyme for 10 min (37° C., 5% $CO_2$) before adding trypsin neutralizing solution (ATCC, Va.), pelletizing cells (200 RCF, 10 min, 0° C.), suspending cells in 10 mL fresh media, counting, and seeding $3\times10^5$ cells in 35 mL of new complete media in a new T-175 culture flask.

β-galactosidase Enzyme

β-galactosidase from *E. coli* was diluted with sterile Dulbecco's Phosphate Buffer Saline (DPBS) to an initial concentration of 5,000 U/mL. Aliquots of this stock were diluted with additional DPBS to a concentration of 500 U/mL and 5 mU/mL. Because of the *E. coli* source for β-galactosidase, samples were filtered with a sterile 0.2 μm syringe filter to guard against potential residual bacteria. Absence of bacteria was confirmed prior to use; filtered samples were plated on an agar plate and incubated for 3 days (37° C., 5% $CO_2$). No bacterial growth was observed from the filtered enzyme.

RAW-Blue Colorimetric Assay

Measurement of RAW-Blue cell activation was performed similarly to manufacturer instructions. For the NF-κB assay, $1\times10^5$ RAW-Blue cells were seeded in an optically clear bottomed 96-well plate in 180 μL of complete assay media (identical to B16 media) at a density of $1\times10^5$ cells/well. For co-culture experiments with RAW-Blue and B16 or β-galactosidase-enriched B16 cells, RAW-Blue cells were seeded at a density of $1\times10^5$ cells/well and were allowed to adhere for 4 h before the addition of the B16 cells, which were seeded at a density of $1\times10^5$ cells/well. For co-culture experiments with RAW-Blue and β-galactosidase-enriched B16 cells, RAW-Blue cells were seeded at a density of $1\times10^5$ cells/well and were allowed to adhere for 4 h before the addition off β-galactosidase-enriched B16 cells, which were seeded at a density of $1\times10^5$ cells/well.

For experiments with β-gal, a stock solution (500 U/mL, where 1 U=1 μmol/min) was used. A final enzymatic activity of 1 U/well was achieved by addition of 2 μL of the 500 U/mL stock solution to each well. Imiquimod or (6) were prepared as 1.15 and 1.49 mg/mL stock solutions, respectively, in DMSO, and were added to the appropriate wells to achieve the specified final concentrations in each experiment ranging from 0.1 to 10 μM. All cell culture experiments were diluted with complete media to a final total volume of 200 μL/well. The cells were allowed to incubate for 16 h (37° C., 5% $CO_2$) before measuring NF-κB transcription by colorimetric assay of alkaline phosphatase. Detection of alkaline phosphatase was performed using p-nitrophenyl phosphate (PNPP) detection media (Fisher) prepared according to manufacturer's instructions (0.50 g PNPP with 100 mL diethanolamine in 400 mL water). In a separate 96-well plate, 180 μL of PNPP was added to each well; to this was added 20 μL of the supernatant from corresponding well plates from the RAW-Blue cell assay. The PNPP assays were incubated for 3 h (37° C., 5% $CO_2$), and the absorbance was measured at 405 nm. Each experiment was performed in hexaplet and a blank was subtracted from all values obtained. This assay was repeated for a later time point of 22 h for samples containing; abrogation of activity persisted.

JAWSII ELISA Protocols

Measurement of JAWSII cytokine production was performed similarly to manufacturer instructions. The cytokines analyzed were IL-12, IL-6, and TNF. For the cytokine assays, $1\times10^5$ JAWSII cells were seeded in an optically clear bottomed 6-well plate in 1 mL of complete assay media (identical to JAWSII growth media) for a density of $1\times10^5$ cells/well. Cells were incubated for 42 h. For co-culture experiments with JAWSII and B16 or β-galactosidase-enriched B16 cells, JAWSII cells were seeded at a density of $1\times10^5$ cells/well and allowed to adhere for 42 h before the addition of B16 cells, which were seeded at a density of $1\times10^5$ cells/well. For co-culture experiments with JAWSII and β-galactosidase-enriched B16 cells, JAWSII cells were seeded at a density of $1\times10^5$ cells/well and allowed to adhere for 42 h before the addition of β-galactosidase-enriched B16 cells, which were seeded at a density of $1\times10^5$ cells/well.

For experiments with β-gal, a stock solution (500 U/mL, where 1 U=1 μmol/min) was used. A final enzymatic activity of 1 U/well was achieved by addition of 2 μL of the 500 U/mL stock solution to each well. Stock solutions of Imiquimod or (6) in DMSO (1.15 and 1.49 mg/mL, respectively) were then added to the appropriate wells to achieve a final concentration of 5 μM. The cells were incubated for 16 h (37° C., 5% $CO_2$) before supernatant was collected. Cells were pelletized (200 RCF, 10 min) and removed. Supernatant was analyzed for cytokines without further dilution according to manufacturer instructions for ELISA. Absorbance was analyzed at 450 nm and standard curves were used to determine absolute cytokine concentrations.

B16 β-Galactosidase-Enrichment Protocol

Murine melanoma cells (B16-F10, $5\times10^6$ cells) were removed from cell culture and pelletized via centrifuge (200 RCF, 0° C., 10 min). The supernatant was removed from the cell pellet, and cells were suspended in 1.5 mL of complete culture media (10% HI-FBS in DMEM) or preservative free FACS solution (10% HI-FBS in DPBS) that was pre-chilled on ice. Next, 15 μL of 0.5 mg/mL biotinylated α-gp-100 antibody (Abcam, UK) was added to the suspended cells, and the suspension was incubated on ice for 30 min with occasional shaking. Cells were then pelletized (200 RCF, 10 min, 0° C.) and washed 4 times each with 10 mL of chilled preservative free FACS solution (10% HI-FBS in DPBS). Washing Procedure: The cell pellet was suspended in 10 mL of FACS and centrifuged (200 RCF, 0° C., 10 min). Supernatant was removed from pellet, and the cells were suspended in subsequent chilled FACS solution for 1 min with constant shaking before this procedure was repeated. After 4 washes, cells were suspended in 1.5 mL of chilled FACS. Avidin-β-gal fusion protein (0.5 mg/mL in DPBS) was added to the cells to a final concentration of 5 μg/mL (15

μL). Cells were incubated on ice for 30 min with occasional shaking. Next, cells were washed 4 times and suspended in FACS before subsequent use in 4-nitrophenyl-β-galactopyranoside (NPG), RAW-Blue, or JAWSII assays. Enzyme enrichment (20-350 pU/cell) was quantified as average increase in enzymatic activity per cell determined by NPG colorimetric assay.

4-Nitrophenyl-β-Galactopyranoside Assay Protocol

After β-galactosidase-enrichment, aliquots of β-galactosidase-enriched melanoma cells in FACS were submitted to NPG assay conditions to quantify enzyme activity. Cells were seeded in an optically clear bottomed 96-well plate at densities ranging from $1\times10^5$ to $5\times10^5$ cells/well. DPBS (175 μL) was added to each well, followed by 25 μL of a 50 nmol/μL NPG solution (1.25 μmol/well). Plates were incubated for 2 h (37° C., 5% $CO_2$), and 70 μL aliquots were analyzed at 405 nm with a FLUOstar Omega (BMG LabTech) plate reader. The resulting data provided a linear correlation between cell density and enzymatic activity which could be extrapolated to provide an average enzymatic activity between 20-350 pU/cell or 2-35 mU/well.

ATB3B-1 Cell Culture Protocol

The AT3B-1 cell line (ATCC CRL-2375, rat prostate epithelial malignant carcinoma) were grown in complete culture media composed of Roswell Park Memorial Institute (RPMI) 1640 medium with 4.5 g/L glucose, 2 mM L-glutamine, 10,000 U/mL penstrep, 10 mM HEPES and supplemented with 10% HI-FBS and 1 μM doxorubicin. Media was changed every 3-4 days omitting the doxorubicin, and cells were passaged once per week. Passaging involved changing media, counting, and seeding 3×105 cells in 35 mL of new complete media in a new T-175 culture flask.

α-Mannosidase Enzyme Cell Culture Protocol

α-Mannosidase from *Canavalia ensiformis* (Jack bean) was used directly from the bottle to make a 1 U/mL stock solution in DPBS. Before administering the enzyme, the solution was filtered through a sterile 0.2 μm syringe filter to yield the working stock solution. 20 μL of the working stock solution was added to wells requiring exogenous enzyme to achieve a 0.1 U/mL α-Mannosidase concentration.

Inverse RAW-Blue Assay Protocol

For inverse RAW-Blue assays, pro-immunostimulant (12) was first converted to Imiquimod by either exogenous α-Mannosidase (0.1 U/well) or via AT3B-1 cell metabolism prior to RAW-Blue exposure. To accomplish this, pro-immunostimulant (12) and controls were dosed at a concentration 10× the desired concentration to be administered to immune cells. For instance, to investigate the effects on RAW-Blue stimulation of a 10 μM dose of pro-immunostimulant (6) the following steps would be taken: First, in an optically clear bottomed 96-well plate, wells were prepared to contain 180 μL of complete AT3B-1 cell media (without doxorubicin) and either α-Mannosidase or the desired AT3B-1 cell density (cells were given a minimum of 60 mins to adhere). Second, a 100 μM dose of (12) in DPBS was administered to the wells and total well volumes were adjusted to 200 μL with complete cell media (without doxorubicin). Cells were incubated (37° C., 5% $CO_2$) for 24-72 h. Third, an additional optically clear bottomed 96-well plate was seeded with RAW-Blue cells at a density of $1\times10^5$ cells/well in 180 μL of complete cell media. Next, 20 μL of AT3B-1 supernatant was added bringing the total volume to 200 μL. For this particular experiment, this resulted in a 1:10 dilution of (12) to 10 μM. Plates were incubated (37° C., 5% $CO_2$) for 18 h before measuring NF-κB transcription by colorimetric assay of secreted alkaline phosphatase.

AT3B-1 Efflux Assay

Protocol for the investigation of AT3B-1 efflux was developed following the procedures laid out in the Multidrug Resistance Direct Dye Efflux Assay kit (Chemicon Int., Temecula, Calif.). Briefly, counted AT3B-1 cells were loaded in cold efflux buffer containing either Imiquimod or rhodamine 123 (Rhod) or both at a concentration of 2.6 mM each. To do this, pelletized cells were suspended in ice cold RPMI media containing 1% FBS and analyte at 2.6 mM for 2 h. Cells were re-pelletized and washed with 2.5 mL media without analyte per $10^6$ cells at 0° C. The wash process was completed two times. Since PGP is not active at 0° C., only analyte taken up by cells in the loading period and subsequently effluxed when incubated (37° C., 5% $CO_2$) will be in the supernatant. Rhod is a known PGP substrate and competes with Imiquimod for efflux from the cell on the time scale measured. We expected to see a diminished immune cell response from AT3B-1 cells loaded with both Imiquimod (2.6 mM) and Rhod (2.6 mM) relative to cells loaded with only Imiquimod (2.6 mM). FIG. 3 shows efflux data acquired from 250 μL supernatant collected at 0, 1, or 24 h of incubation time and subsequently measured by an inverse RAW-Blue assay.

It should be emphasized that the above-described embodiments and following specific examples of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

We claim:

1. A compound of formula (II),

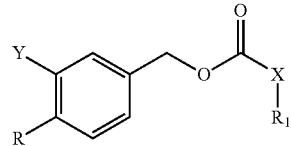

wherein
R is selected from the group consisting of

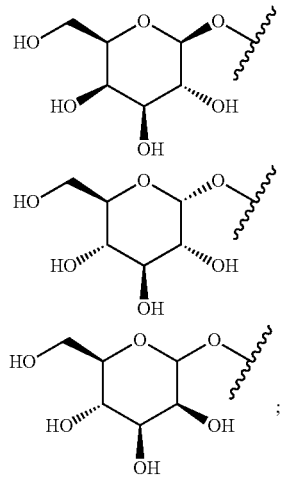

R1 consists of

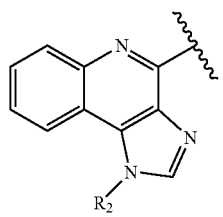

wherein, R2 is alkyl, substituted alkyl, alkenyl, alkynyl, and substituted alkynyl;
X is O, S, N, or CH2; and
Y is —OH, —OR7, —OCOR7 and —NO$_2$, wherein R7 is an alkyl or substituted alkyl,
or a pharmaceutically acceptable salt thereof.

2. A compound of claim 1, wherein
R is

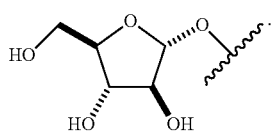 [SMILES: *O[C@H]1O[C@H](CO)[C@@H](O)[C@@H]1O]

3. A compound of claim 1, wherein R1 is a pharmaceutically acceptable salt of pyranoside, serine, or glutamate.

4. The compound of claim 1 wherein the compound has the formula,

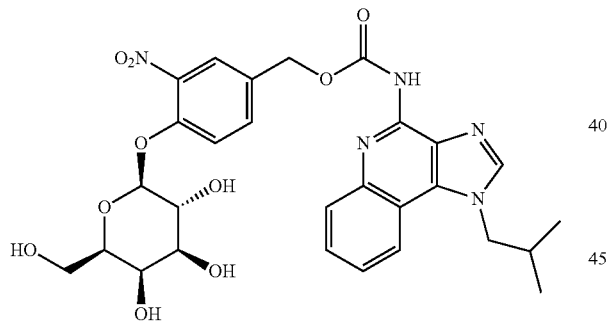

or a pharmaceutically acceptable salt thereof.

5. The compound of claim 1 wherein the compound has the formula,

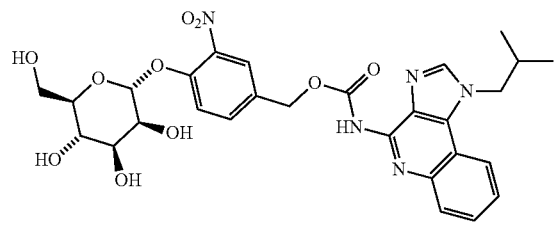 [SMILES: CC(C)Cn1cnc2c(NC(=O)OCc3ccc(O[C@H]4O[C@H](CO)[C@@H](O)[C@H](O)[C@@H]4O)c([N+](=O)[O-])c3)nc3ccccc3c21]

or a pharmaceutically acceptable salt thereof.

6. A compound of the formula (I),

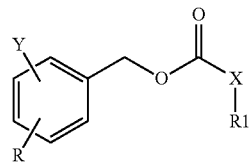

or a pharmaceutically acceptable salt thereof, wherein
R is consisting of pyranosides, furanosides, and mannosides;
R1 is selected from the group consisting of

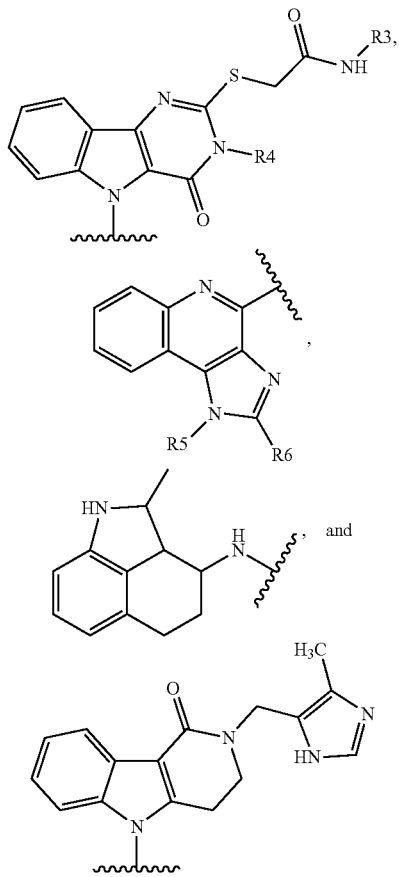

where R3 is aryl, substituted aryl, heteroaryl, substituted alkyl, akynyl, substituted and substituted alkynyl; R4 is aryl, substituted aryl, and heteroaryl; R5 is aryl, substituted aryl, alkyl, and substituted alkyl; and R6 is alkyl, substituted alkyl, alkynyl, and substituted alkynyl;
X is O, S, N, or CH$_2$; and
Y is one or more electron density modifying groups which may be the same or different if more than one Y is present on the benzene ring, and where the electron density modifying groups are selected from —OH, —OR$_7$, —OCOR$_7$ and —NO$_2$, wherein R7 is an alkyl or substituted alkyl.

* * * * *